(12) United States Patent
Czernik

(10) Patent No.: US 9,918,717 B2
(45) Date of Patent: Mar. 20, 2018

(54) PIVOT MECHANISM FOR SURGICAL DEVICE

(71) Applicant: Covidien LP, Mansfield, MA (US)

(72) Inventor: Roman Czernik, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 423 days.

(21) Appl. No.: 14/661,001

(22) Filed: Mar. 18, 2015

(65) Prior Publication Data

US 2016/0270788 A1    Sep. 22, 2016

(51) Int. Cl.
*A61B 17/072* (2006.01)
*A61B 17/10* (2006.01)
*A61B 17/068* (2006.01)
*A61B 17/29* (2006.01)
*A61B 17/00* (2006.01)

(52) U.S. Cl.
CPC .......... *A61B 17/105* (2013.01); *A61B 17/068* (2013.01); *A61B 17/072* (2013.01); *A61B 17/07207* (2013.01); *A61B 2017/00473* (2013.01); *A61B 2017/00477* (2013.01); *A61B 2017/07214* (2013.01); *A61B 2017/07228* (2013.01); *A61B 2017/07242* (2013.01); *A61B 2017/07271* (2013.01); *A61B 2017/07278* (2013.01); *A61B 2017/2927* (2013.01); *A61B 2017/2947* (2013.01)

(58) Field of Classification Search
CPC ............ A61B 17/07207; A61B 17/068; A61B 17/072; A61B 17/115; A61B 2017/07214; A61B 2017/07228; A61B 2017/07242; A61B 2017/07271

USPC .......... 227/19, 175.1, 176.1, 180.1; 606/139, 606/153, 219
See application file for complete search history.

(56) References Cited

U.S. PATENT DOCUMENTS

| | | | |
|---|---|---|---|
| 3,079,606 | A | 3/1963 | Bobrov et al. |
| 3,490,675 | A | 1/1970 | Green et al. |
| 3,499,591 | A | 3/1970 | Green |
| 3,777,538 | A | 12/1973 | Weatherly et al. |
| 3,882,854 | A | 5/1975 | Hulka et al. |
| 4,027,510 | A | 6/1977 | Hiltebrandt |
| 4,086,926 | A | 5/1978 | Green et al. |
| 4,241,861 | A | 12/1980 | Fleischer |
| 4,244,372 | A | 1/1981 | Kapitanov et al. |
| 4,429,695 | A | 2/1984 | Green |
| 4,505,414 | A | 3/1985 | Filipi |

(Continued)

FOREIGN PATENT DOCUMENTS

| | | |
|---|---|---|
| AU | 198654765 | 9/1986 |
| CA | 2773414 A1 | 11/2012 |

(Continued)

OTHER PUBLICATIONS

European Search Report EP16160831.0-1654 dated Jul. 25, 2016.

*Primary Examiner* — Scott A. Smith

(57) ABSTRACT

A pivot mechanism for use with a surgical device includes a first jaw member, a second jaw member, and a pivot pin. The first jaw member includes at least one circular aperture. The second jaw member includes at least one square-like aperture. The pivot pin is configured to engage the at least one circular aperture of the first jaw member and the at least one square-like aperture of the second jaw member such that the first jaw member is pivotably coupled to the second jaw member.

16 Claims, 26 Drawing Sheets

(56) References Cited

U.S. PATENT DOCUMENTS

| | | |
|---|---|---|
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |

(56) References Cited

U.S. PATENT DOCUMENTS

| | | |
|---|---|---|
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicola |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |

(56) References Cited

U.S. PATENT DOCUMENTS

| | | |
|---|---|---|
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |

(56) References Cited

U.S. PATENT DOCUMENTS

| | | |
|---|---|---|
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Bohail et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scirica |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |

(56) References Cited

U.S. PATENT DOCUMENTS

| | | |
|---|---|---|
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |

(56) References Cited

U.S. PATENT DOCUMENTS

| | | |
|---|---|---|
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |

(56) References Cited

U.S. PATENT DOCUMENTS

| | | |
|---|---|---|
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |

(56) References Cited

U.S. PATENT DOCUMENTS

| | | |
|---|---|---|
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2013/0240604 A1* | 9/2013 | Knodel ............... A61B 17/068 |
| | | 227/180.1 |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |

(56) References Cited

FOREIGN PATENT DOCUMENTS

| | | |
|---|---|---|
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1813197 A2 | 8/2007 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51-149985 | 12/1976 |
| JP | 2001-87272 | 4/2001 |
| SU | 659146 A1 | 4/1979 |
| SU | 728848 A1 | 4/1980 |
| SU | 980703 A1 | 12/1982 |
| SU | 990220 A1 | 1/1983 |
| WO | 08302247 | 7/1983 |
| WO | 89/10094 A1 | 11/1989 |
| WO | 9210976 A1 | 7/1992 |
| WO | 9308754 A1 | 5/1993 |
| WO | 9314706 A1 | 8/1993 |
| WO | 2004/032760 A2 | 4/2004 |
| WO | 2009071070 A2 | 6/2009 |

\* cited by examiner

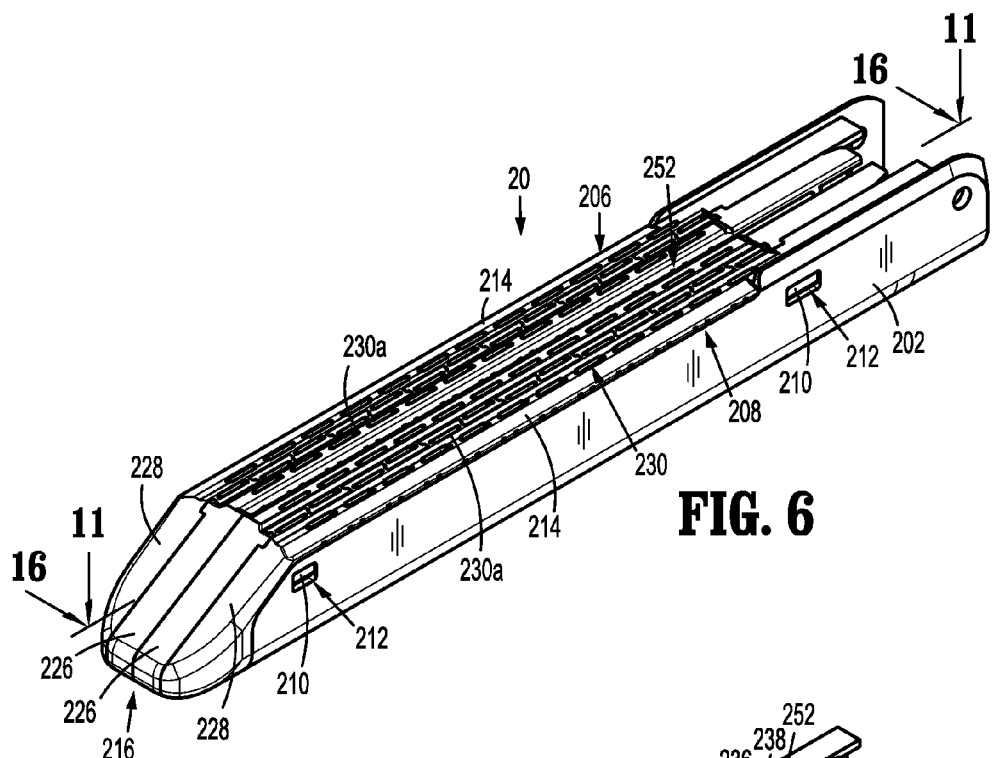
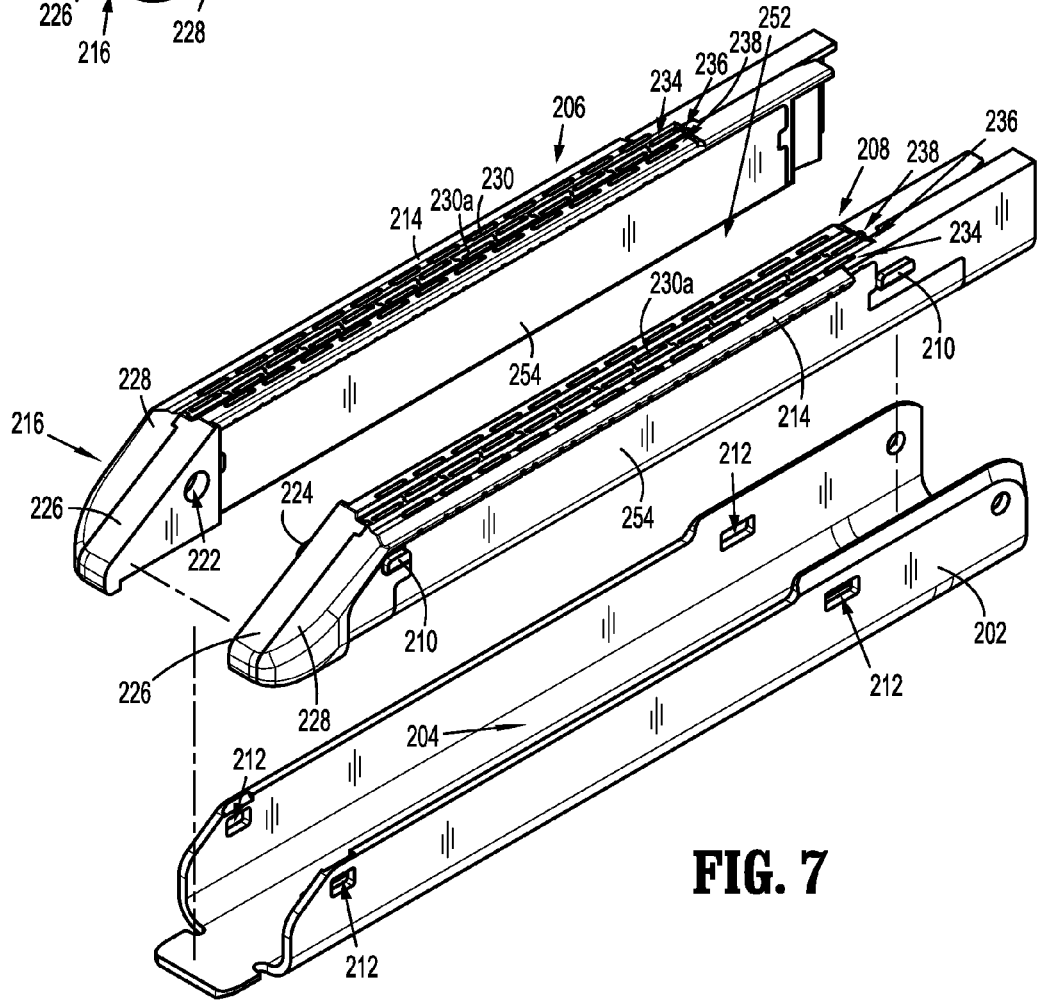

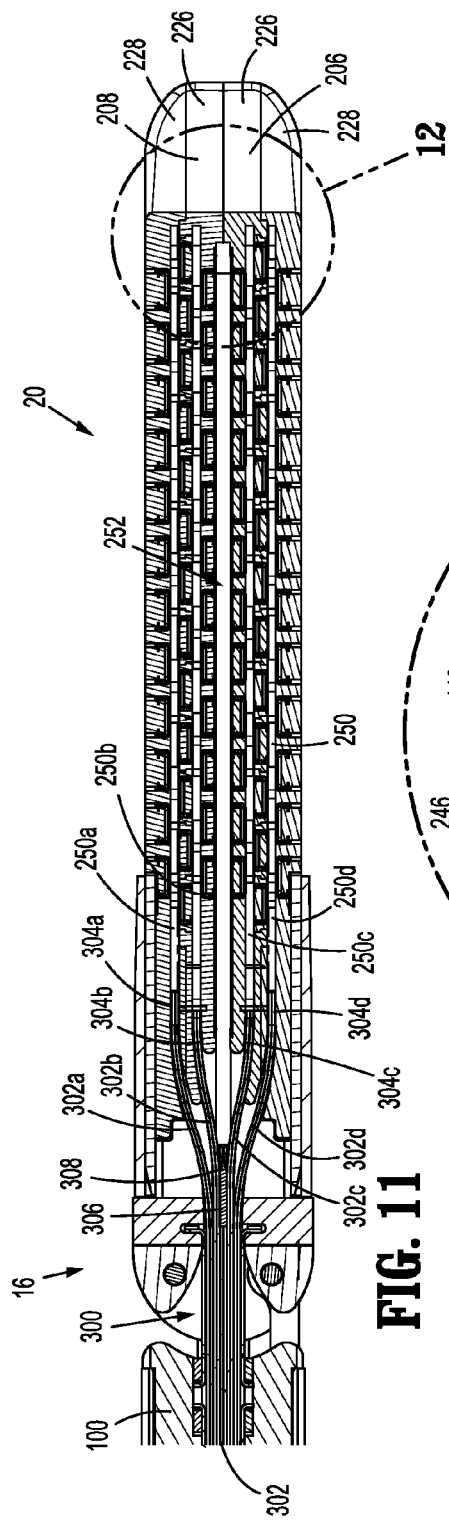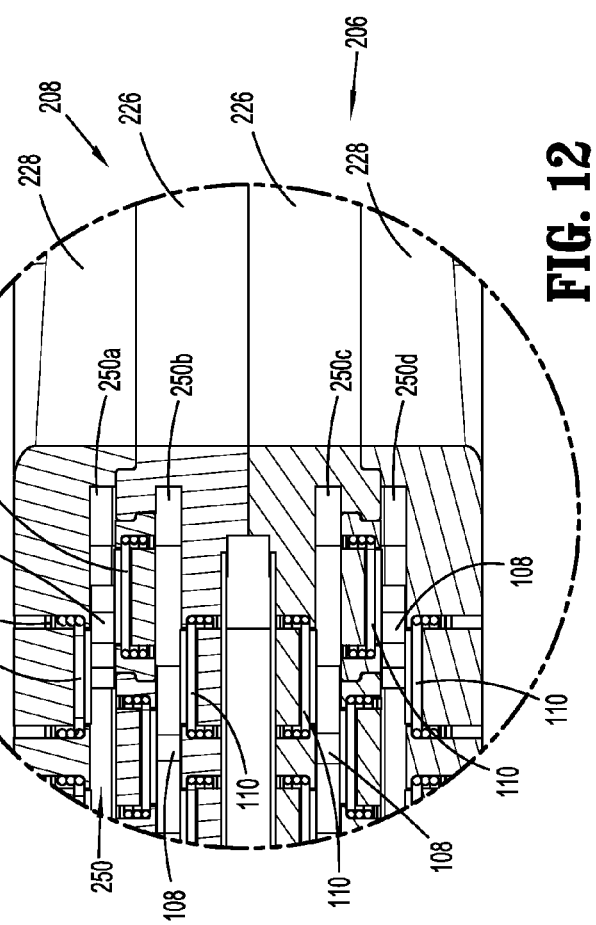
FIG. 11
FIG. 12

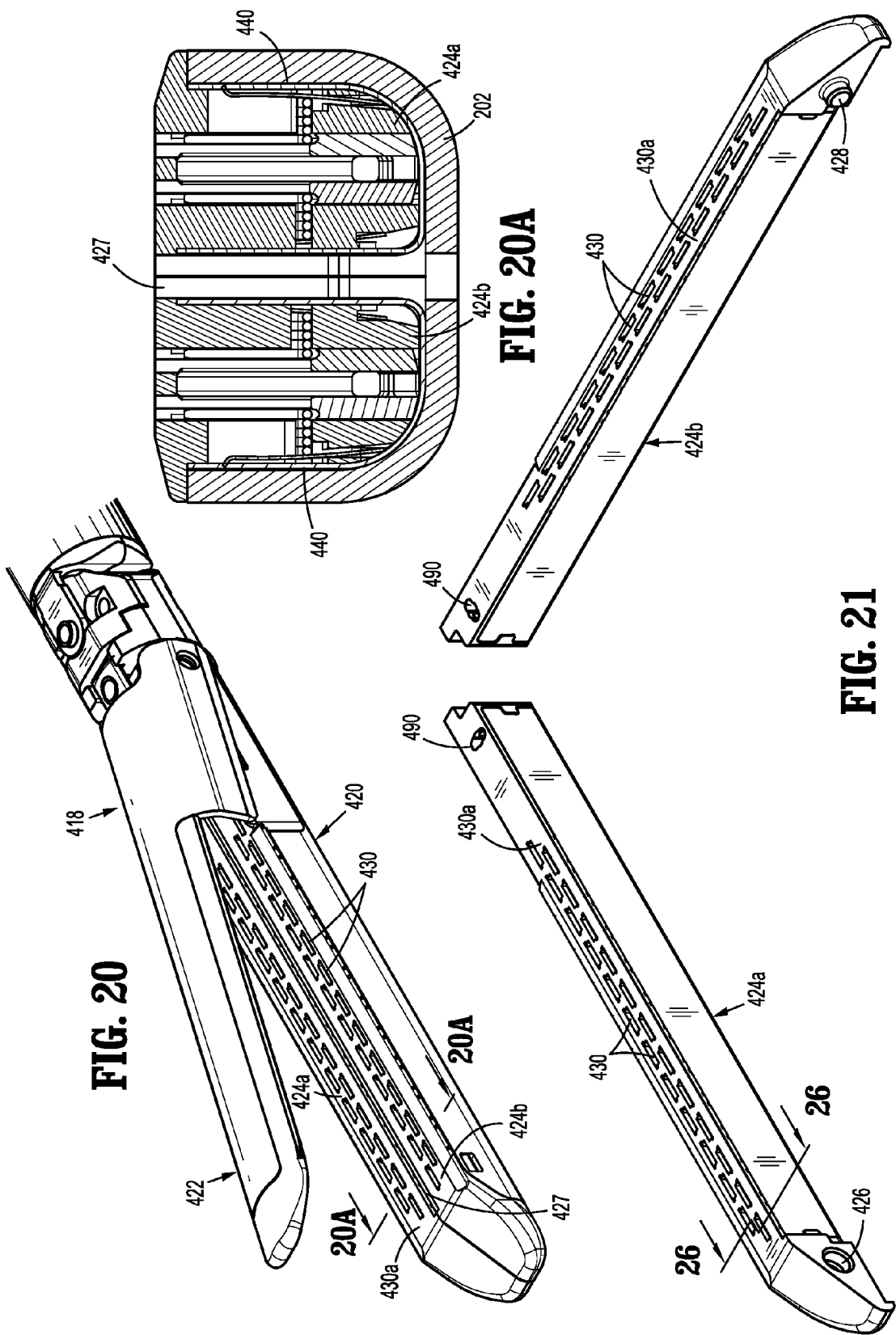

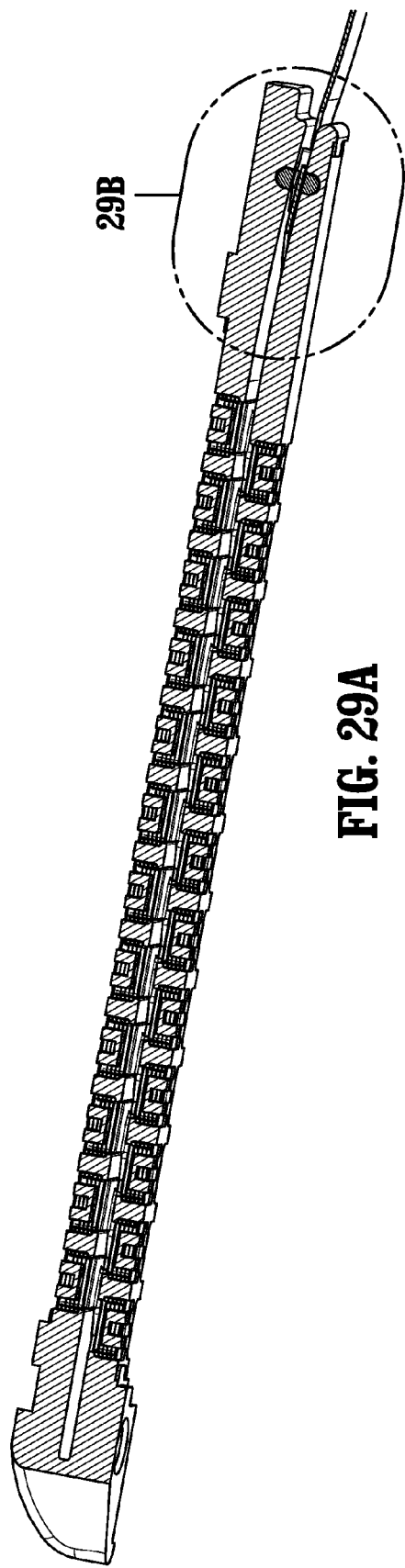
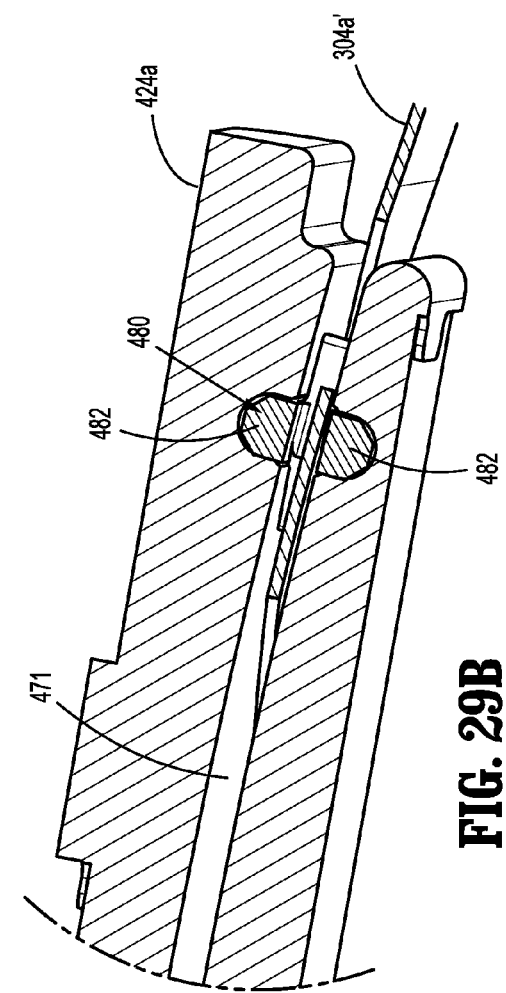
FIG. 29A
FIG. 29B

PIVOT MECHANISM FOR SURGICAL DEVICE

BACKGROUND

Technical Field

This application relates to a surgical device, and more particularly, to a pivot mechanism for use with a surgical device, wherein the pivot mechanism includes a pivot pin, a cartridge aperture and an anvil aperture.

Background of Related Art

Surgical devices that grasp and clamp tissue between opposing jaw structure and, subsequently join cut and fasten the tissue are well known in the art. Such devices can include two elongated members which are used to capture or clamp tissue. Typically, one of the members carries a staple cartridge which houses a plurality of staples while the other member has an anvil that defines a surface for forming the staples as the staples are driven from the staple cartridge. Generally, the stapling operation is effected by a cam bar, a drive sled or other similar mechanism having a cam member that travels longitudinally through the staple cartridge and acts upon staple pushers to sequentially eject the staples from the staple cartridge. The cam member is moved into engagement with the staple pushers which are located within the grooves and are positioned in such a manner so as to be contacted by the longitudinally moving cam member to effect ejection of the staples from the staple cartridge of the surgical device.

Typically, surgical stapling devices include a staple cartridge or loading unit (e.g., a disposable loading unit) that must be replaced after each time the stapling device is fired for subsequent reuse of the device. In endoscopic or laparoscopic procedures wherein surgery is performed through small incisions or through narrow cannulas inserted through the small incisions in the skin, replacement of the cartridge or loading unit requires removal of the stapling device from the incision or cannula, replacement of the cartridge or loading unit and reinsertion of the stapling device into the incision or cannula. An example of an endoscopic surgical stapling device is disclosed, for example, in U.S. Pat. No. 8,070,033 to Milliman et al., the entire contents of which is incorporated herein by reference.

It would be beneficial to provide a surgical device including a pivot mechanism to facilitate manufacture, assembly and operation of pivoting jaw members of the surgical device.

SUMMARY

The present disclosure relates to a pivot mechanism for use with a surgical device. The pivot mechanism includes a first jaw member, a second jaw member, and a pivot pin. The first jaw member includes at least one circular aperture. The second jaw member includes at least one square-like aperture. The pivot pin is configured to engage the at least one circular aperture of the first jaw member and the at least one square-like aperture of the second jaw member such that the first jaw member is pivotably coupled to the second jaw member.

In disclosed embodiments, the at least one circular aperture of the first jaw member includes two circular apertures. It is further disclosed that the at least one square-like aperture of the second jaw member includes two square-like apertures.

In embodiments of the present disclosure, the at least one square-like aperture of the second jaw member includes four linear walls with adjacent linear walls interconnected by a rounded portion.

The present disclosure also includes embodiments where the pivot pin includes a head at a proximal portion, a tip at a distal portion, and a body between the head and the tip. An entirety of the body includes a constant outer diameter. It is disclosed that the body is in contact with the tip, and that an entirety of the tip is conical.

In disclosed embodiments, the at least one circular aperture of the first jaw member is disposed laterally outward of the at least one square-like aperture of the second jaw member.

It is further disclosed that the first jaw member is an anvil assembly and the second jaw member is a cartridge assembly.

The present disclosure also relates to a surgical device comprising a handle assembly, an elongated body extending distally from the handle assembly, a loading unit disposed adjacent a distal end of the elongated body and including a first jaw member having a circular aperture, and a second jaw member having a square-like aperture, and a pivot pin disposed in mechanical cooperation with the circular aperture and the square-like aperture.

In disclosed embodiments, a body of the pivot pin is disposed in mechanical cooperation with the square-like aperture, and wherein an entirety of the body has a cylindrical configuration.

It is further disclosed that the square-like aperture of the second jaw member includes four linear walls with adjacent linear walls interconnected by a rounded portion.

The present disclosure also includes embodiments where the pivot pin includes a head at a proximal portion, a tip at a distal portion, and a body disposed therebetween. An entirety of the body has a uniform outer diameter.

In disclosed embodiments, the circular aperture of the first jaw member is disposed laterally outward of the square-like aperture of the second jaw member.

It is further disclosed that the first jaw member is an anvil assembly and the second jaw member is a cartridge assembly.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 6 is a perspective view of the cartridge assembly of the disposable loading unit of FIG. 3;

FIG. 7 is an exploded view of the cartridge assembly of FIG. 6, illustrating a pair of cartridges and a carrier;

FIG. 11 is a cross-sectional view of the cartridge assembly of FIG. 6, taken along section line 11-11;

FIG. 12 is an enlarged view of the distal end portion of the cartridge assembly of FIG. 11 indicated by the area of detail 12;

FIG. 20 is a side perspective view of an alternate embodiment of the tool assembly of the presently disclosed surgical stapling apparatus;

FIG. 20A is a cross-sectional view taken along section line 20A-20A of FIG. 20;

FIG. 21 is a side perspective view of a cartridge body of the cartridge assembly of the tool assembly shown in FIG. 20 with the cartridge separated into two body halves;

FIG. 29A is a cross-sectional view taken along section line 29A-29A of FIG. 29;

FIG. 29B is an enlarged view of the indicated area of detail shown in FIG. 29A;

DETAILED DESCRIPTION OF EMBODIMENTS

Embodiments of the presently disclosed surgical stapling apparatus will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
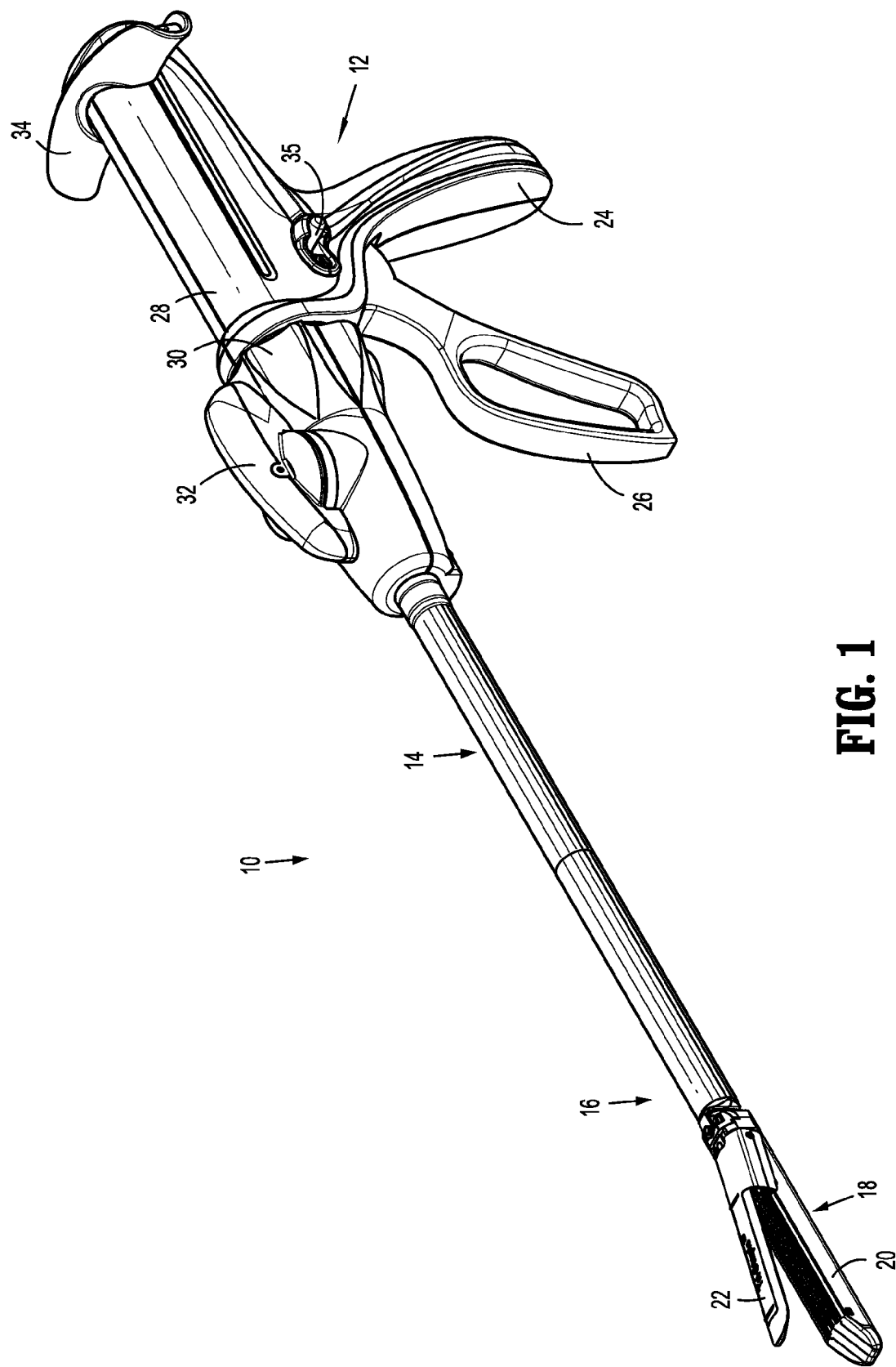
FIG. 1 is a perspective view of an exemplary surgical stapling apparatus according to the present disclosure.
Figure 2:
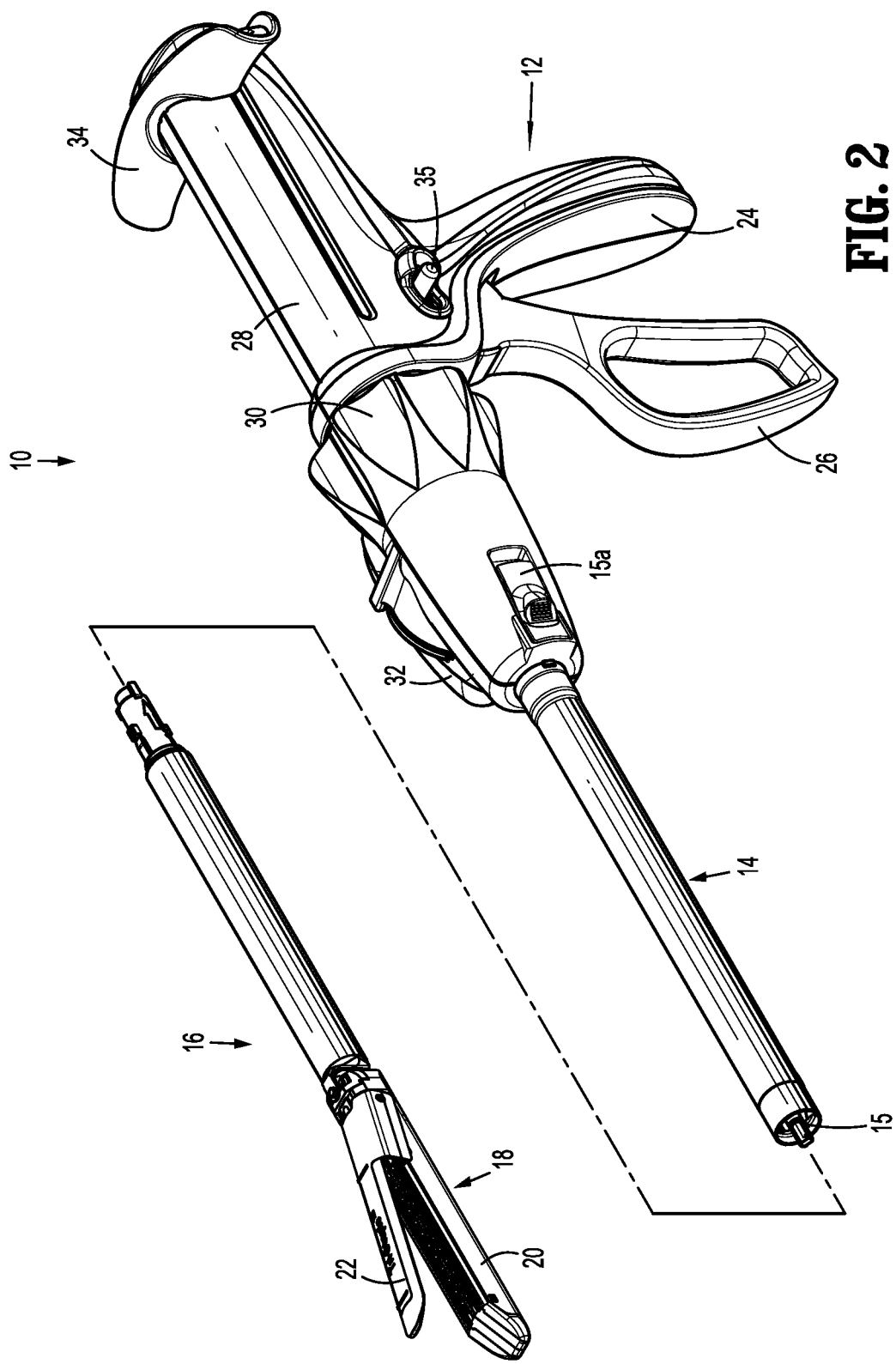
FIG. 2 is a perspective view of the surgical stapling apparatus of FIG. 1 with the disposable loading unit detached and the shaft rotated 90°.

FIGS. 1 and 2 illustrate one embodiment of the presently disclosed surgical stapling device 10. Briefly, surgical stapling device 10 includes a handle assembly 12, an elongated body 14 and a loading unit (e.g., disposable loading unit) 16. The loading unit 16 is releasably secured to the distal end of the elongated body 14 and includes a tool assembly 18. The tool assembly 18 includes a cartridge assembly 20 which houses a plurality of staples and an anvil assembly 22 which is pivotally secured in relation to the cartridge assembly 20 between spaced and approximated positions. The handle assembly 12 includes a stationary handle 24, a movable handle 26 and a barrel portion 28. A rotatable member 30 is rotatably supported on a distal end of the barrel position 28. The rotatable member 30 supports a proximal end of the elongated body 14 and is rotatable in relation to the barrel portion 28 of the handle assembly 12 to effect rotation of the body 14 and the tool assembly 18 in relation to the handle assembly 12. The rotatable member 30 supports an articulation lever 32, and the barrel portion 28 supports a retraction member 34 and a firing release button 35. The handle assembly 12 is described in detail in, e.g., U.S. Pat. No. 8,070,033 to Milliman et al. ("the '033 patent") which is incorporated herein by reference in its entirety.

Referring to FIG. 2, the body 14 supports a control rod 15 which is coupled to a coupling member 307 (FIG. 14) of a firing cam assembly 300 of the loading unit 16 which will be discussed in further detail below. A release switch 15a is provided on the rotatable member 30 of the handle assembly 12 to facilitate disengagement of the loading unit 16 from the elongated body 14. For a more detailed description of the body 14, see the '033 patent which has been incorporated herein by reference.

Figure 3:
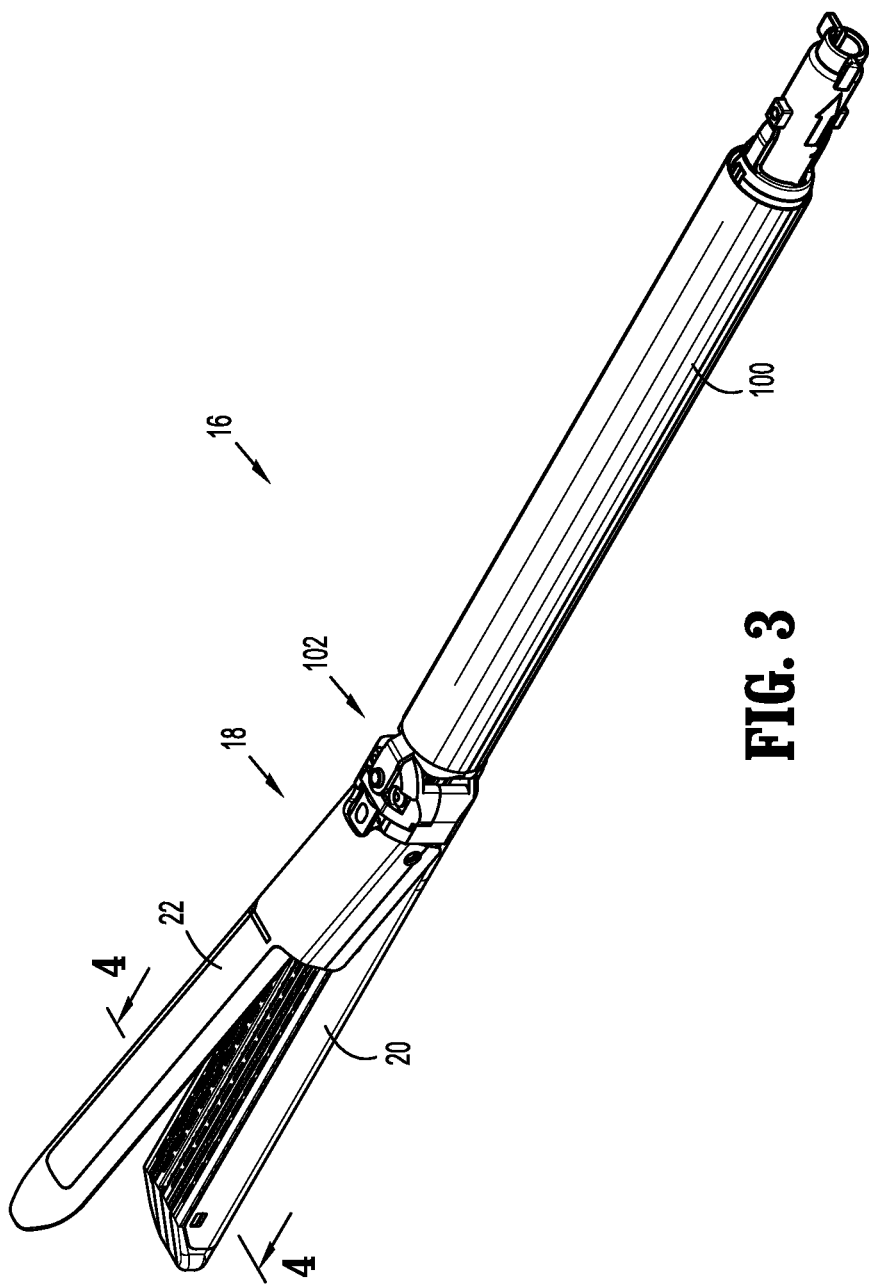
FIG. 3 a perspective view of the disposable loading unit of the surgical stapling apparatus of FIG. 1.

Referring to FIG. 3, the loading unit 16 includes a proximal housing portion 100 which is adapted to releasably engage the distal end of body portion 14 (FIGS. 1 and 2). A mounting assembly 102 is pivotally secured to the distal end of housing portion 100, and is configured to engage and support the proximal end of tool assembly 18 such that pivotal movement of mounting assembly 102 about an axis perpendicular to the longitudinal axis of housing portion 100 effects articulation of tool assembly 18. See, e.g., the '033 patent for a detailed description of a mounting assembly 102.

Referring to FIGS. 3-10, tool assembly 18 includes a cartridge assembly 20 and an anvil assembly 22 pivotally connected to the cartridge assembly 20. The anvil assembly 22 defines a plurality of staple forming pockets 22a (FIG. 18), each of which is being positioned to receive a staple from the cartridge assembly 20. An example of a suitable anvil assembly 22 is described in detail in the '033 patent. Cartridge assembly 20 includes a carrier 202 which defines an elongated support channel 204 (FIG. 7) and receives a pair of staple cartridges 206, 208. Corresponding tabs 210 and slots 212 formed along staple cartridges 206, 208 and elongated support channel 204, respectively, function to retain staple cartridges 206, 208 within support channel 204. A support strut 214 formed along each staple cartridge 206, 208 is positioned to rest on a side wall of carrier 202 to stabilize staple cartridges 206, 208 within support channel 204.

With reference now to FIGS. 6 and 7, staple cartridges 206, 208 are configured to couple together at a distal end portion 216 of each of the cartridges 206, 208 to define a central longitudinal slot 252. The slot 252 facilitates passage of a knife assembly 308 (FIG. 14) through the cartridge assembly 20. An inner hole 222 formed on a surface of the distal end portion 216 of one of staple cartridges 206, 208 is configured to receive an inner tab 224 formed on a surface of the distal end portion 216 of the other of staple cartridges 206, 208. Inner hole 222 and inner tab 224 function to align staple cartridges 206, 208 when coupled together. Inner hole 222 and inner tab 224 in conjunction with tabs 210, slots 212, and struts 214 also function to maintain staple cartridges 206, 208 in a longitudinally fixed position within the elongated support channel 204 of carrier 202.

Figure 8:
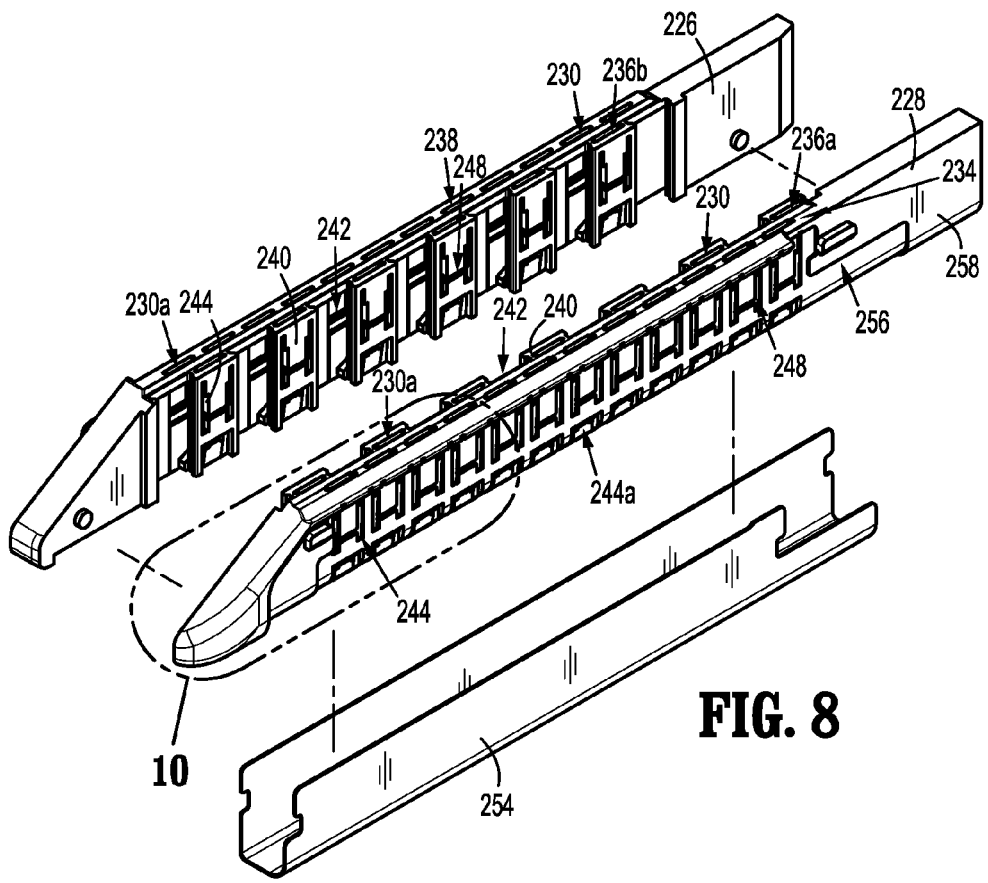
FIG. 8 is an exploded view of one of the cartridges of FIG. 7, illustrating two cartridge halves and a cartridge support channel.

Each staple cartridge 206, 208 includes an inner half and an outer half. FIG. 8 illustrates the inner and outer halves 226 and 228 of staple cartridge 208. We note that the inner and outer halves of staple cartridge 206 are mirror images of halves 226 and 228 and are not specifically described herein. The inner and outer halves 226 and 228, respectively, are configured to be coupled together. Each half 226, 228 includes retention slots 230 formed therein for receiving a plurality of staples 110 and pushers 108. Each of the staples 110 includes a pair of legs 112 having tips 110d and a backspan 110e. Retention slots 230 are aligned in rows, so that when inner half 226 and outer half 228 are coupled together, three rows of retention slots 230 are defined by each of the staple cartridges 206, 208. It is contemplated that staple cartridges 206, 208 may include fewer rows or additional rows of retention slots 230.

Outer half 228 of the staple cartridge 208 includes a first row 234 of retention slots 230 and at least a portion 236a of a second row 236 of retention slots 230. Inner half 226 of the staple cartridge 208 includes a third row 238 or retention slots 230 and at least a remaining portion 236b of the second row 236 of retention slots 230. When outer half 228 and inner half 226 are coupled together, the second row 236 of retention slots 230 is defined in part by each of portions 236a and 236b of inner half 226 and outer half 228 of the staple cartridge 208. In one embodiment, portions 236a and 236b of inner half 226 and outer half 228 of the staple cartridge 208 alternately define the retention slots 230 of second row 236 as illustrated in FIG. 8.

Each of inner half 226 and outer half 228 of the staple cartridge 208 includes a plurality of flanges 240 and a plurality of channels 242. Each flange 240 defines a retention slot 230 of the second row 236. Channels 242 are configured to receive flanges 240 when the inner half 226 is coupled to the outer half 228 of the staple cartridge 208 such that the retention slots 230 of the second row 236 are longitudinally aligned. Channels 242 and flanges 240 may alternate along the length of each of inner half 226 and outer half 228, as illustrated in FIG. 8. Alternatively, retention slots 230 of flanges 240 of each of inner and outer halves 226 and 228 may be slightly offset from a longitudinal axis such that retention slots 230 of flanges 240 of respective inner and outer halves 226 and 228 are not substantially longitudinally aligned.

Referring now to FIGS. 6-8, each cartridge 206, 208 includes a cartridge support channel 254 dimensioned and configured to receive inner and outer halves 226 and 228. Cartridge support channel 254 is configured to maintain inner and outer halves 226 and 228 in engagement in longitudinal alignment with one another. Inner and outer halves 226 and 228 include recessed sections 256 dimensioned and configured for receiving cartridge support channel 254 such that cartridge support channel 254 is substantially aligned with side surfaces 258 of inner and outer halves 226 and 228. This assists in maintaining inner and outer halves 226, 228 coupled together without adding additional width to each cartridge 206, 208 thereby maintaining a minimal width of the overall cartridge assembly 20.

Referring again to FIG. 4, in embodiments, the cartridges 206, 208 each include a tissue contacting surface 104 that is stepped. For example, an outer tissue contacting surface 104a, an intermediate tissue contacting surface 104b, and an inner tissue contacting surface 104c form a stepped configuration. Each tissue contacting surface 104a-104c has a different height from one another as measured from a bottom surface 106 of support channel 254. Specifically, tissue contacting surfaces 104a-104c are planar surfaces that are substantially parallel to one another, but are not co-planar with one another. A first wall surface interconnects tissue contacting surfaces 104a and 104b, while a second wall surface interconnects tissue contacting surfaces 104b and 104c. The first and second wall surfaces are planar structures wherein each wall surface defines an axis with respect to the planes defined by the tissue contacting surfaces 104a-104c. In one embodiment, inner tissue contacting surface 104c is defined on inner half 226 of each cartridge 206, 208, outer tissue contacting surface 104a is defined on outer half 228 of each cartridge 206, 208, and intermediate tissue contacting surface 104b is defined by the flanges 240 of inner half 226 and outer half 228 when inner and outer halves 226, 228 are coupled together.

Figure 4:
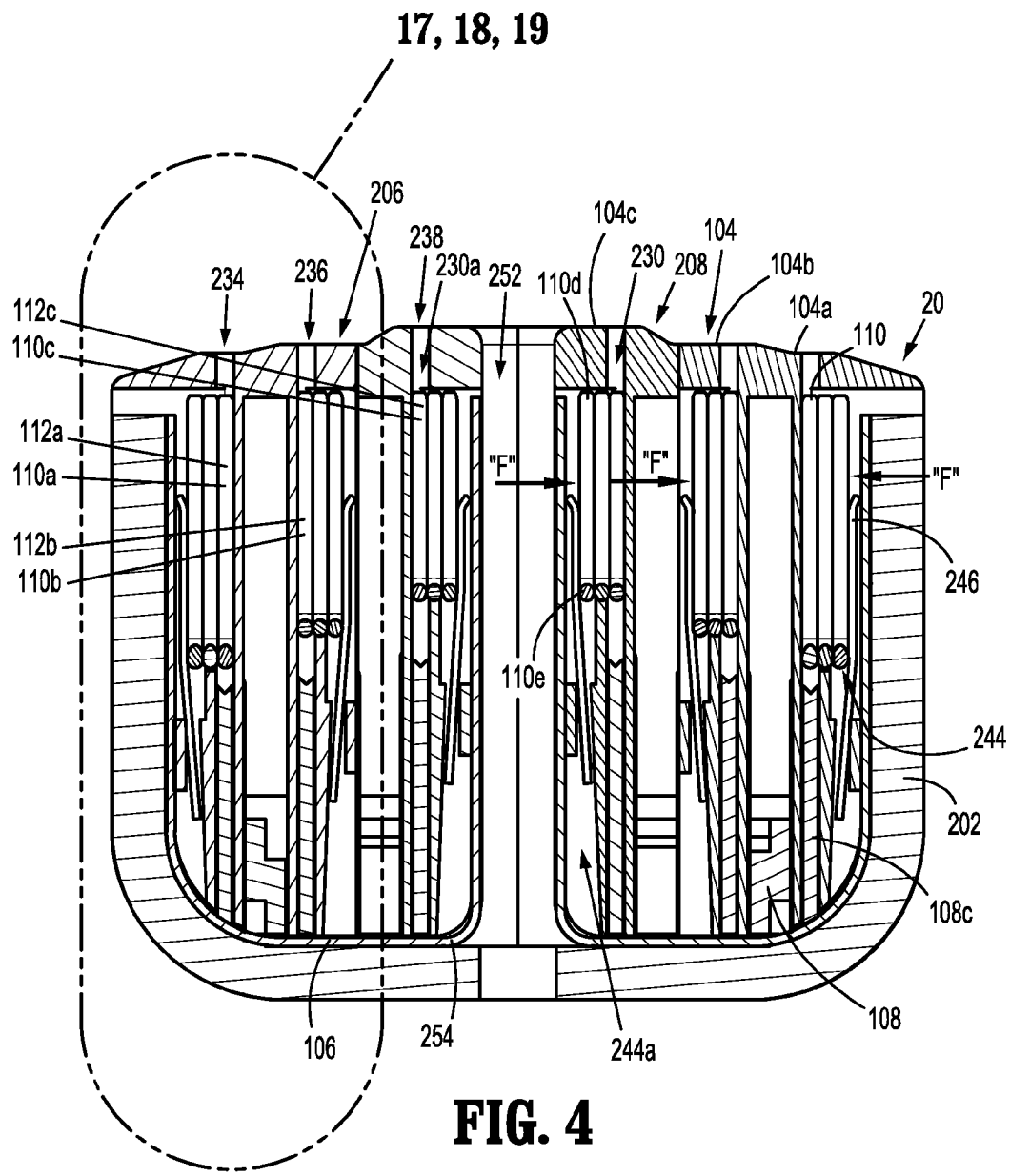
FIG. 4 is a cross-sectional view of the disposable loading unit of FIG. 3 taken along section line 4-4.

Inner tissue contacting surface 104c has the greatest height, outer tissue contacting surface 104a has the least height, and intermediate tissue contacting surface 104b has a height between the heights of outer and inner tissue contacting surfaces 104a, 104c (see FIG. 4). While tissue contacting surfaces 104a-104c are shown as increasing in height from outer most tissue contacting surface 104a to inner most tissue contacting surface 104c, it is within the scope of the present disclosure that the heights of each tissue contacting surface can vary depending on the particular surgical procedure. For example, tissue contacting surfaces 104a-104c can increase in height from the inner most tissue contacting surface 104c to the outer most tissue contacting surface 104a, the intermediate tissue contacting surface 104b can have the greatest height, the intermediate tissue contacting surface 104b can have the least height, or at least two of tissue contacting surfaces 104a-104c can have the same height.

As seen in FIG. 4, each row retention slots 230, 234, 236, 238 may include staples 110 having different sizes. For example, legs 112a of surgical staples 110a disposed in retention slots 230 of first row 234 may have a first leg length, legs 112b of surgical staples 110b disposed in retention slot 230 of second row 236 may have a second leg length, and legs 112c of surgical staples 110c disposed in retention slot 230 of third row 238 may have a third leg length. In particular, surgical staples 110a-110c increase in height from the inner most row 238 to the outer most row 234 of each cartridge. In one embodiment, legs 112c of surgical staples 110c have a leg length of about 2.3 mm, legs 112b of surgical staples 110b have a leg length of about 3.5 mm, and legs 112a of surgical staples 110a have a leg length of about 4.1 mm. As such, inner tissue contacting surface 104c has the greatest height and retains surgical staples 110c having the shortest leg lengths, and outer tissue contacting surface 104a has the least height and retains surgical staples 110a having the longest leg lengths. Tissue contacting surface 104 step progressively downward at intermediate tissue contacting surface 104b and then again at outer tissue contacting surface 104a. It is envisioned and within the scope of the present disclosure that any number of arrangements are possible. In any of the embodiments disclosed herein, the cartridge or cartridges can include staples of different sizes or the cartridge or cartridges can have staples that are all of the same size. Further details of surgical instruments where tissue contacting surfaces increase in height from an outer most tissue contacting surface to an inner most tissue contacting surface, and where surgical staples increase in height from an inner most row to an outer most row is disclosed, for example, in U.S. Pat. No. 7,726,538 to Holsten et al., the entire contents of which is incorporated herein by reference.

Figure 5:
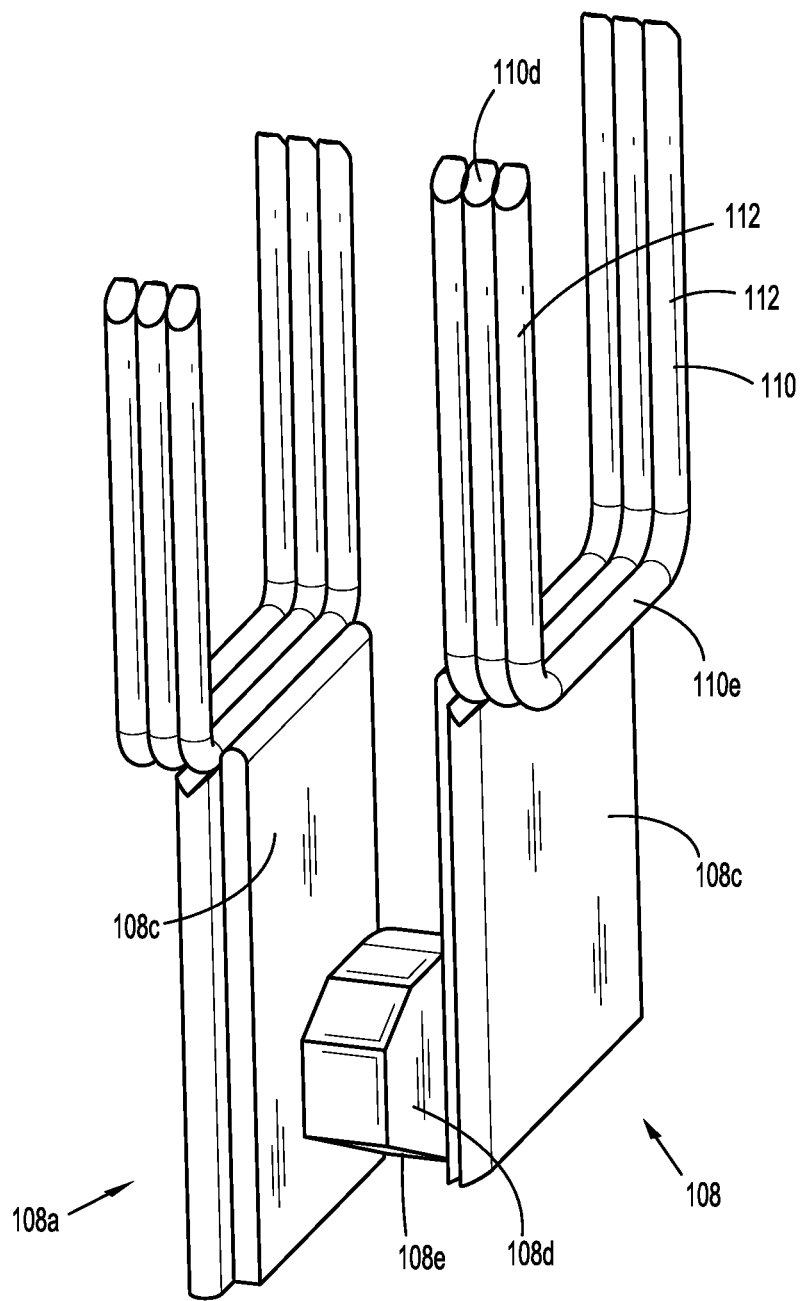
FIG. 5 is a perspective view of a two plate pusher in accordance with the present disclosure.
Figure 9:
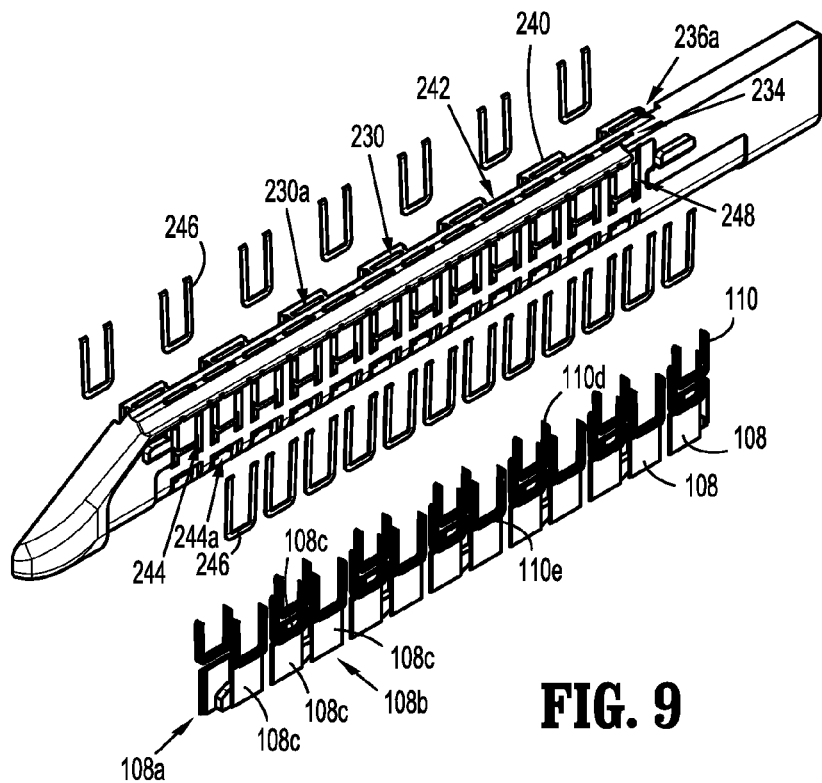
FIG. 9 is an exploded view of one of the cartridge halves of FIG. 8, illustrating the pushers, biasing members and staples removed.
Figure 10:
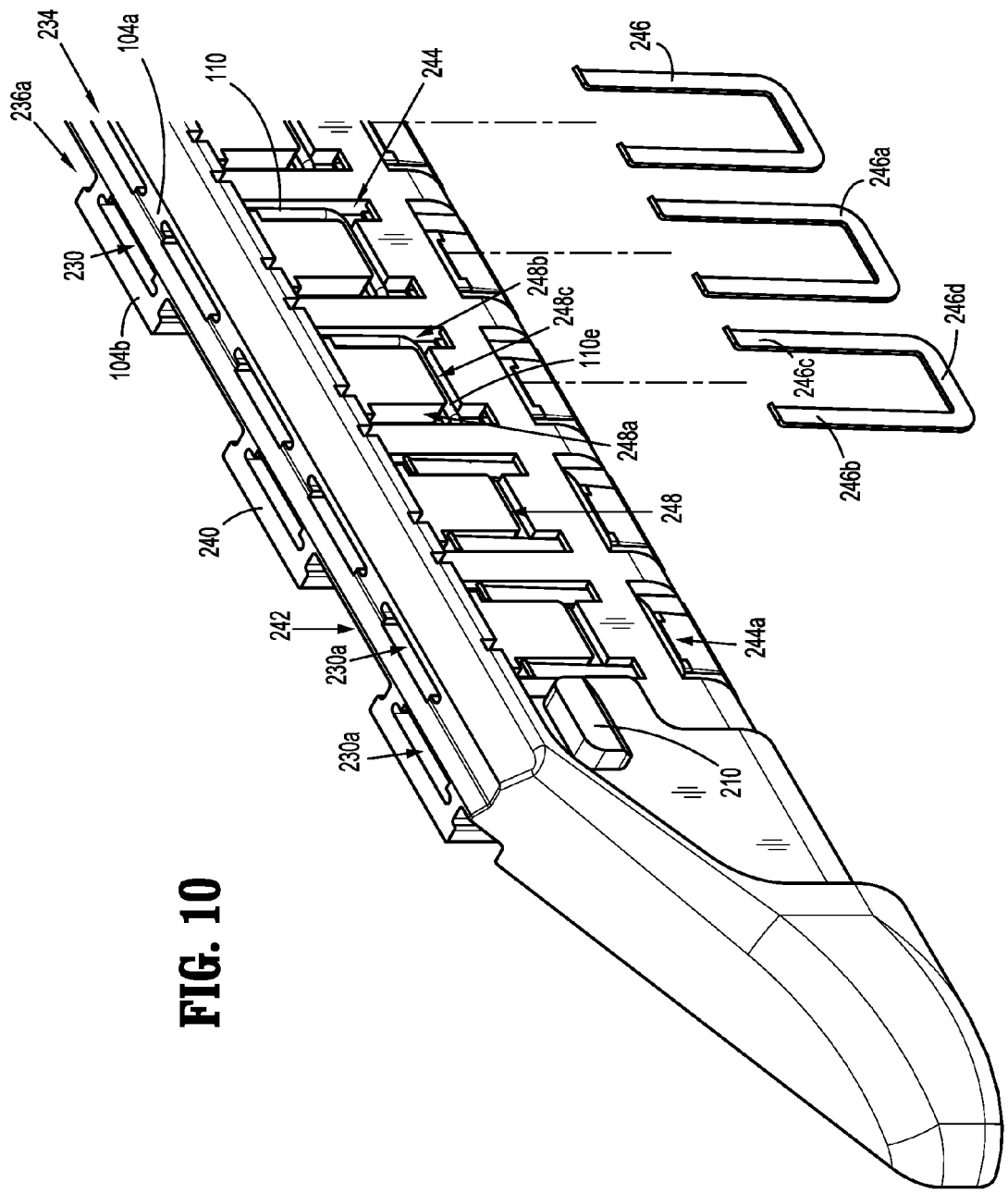
FIG. 10 is an enlarged, partially exploded, view of the distal end of one of the cartridge halves of FIG. 8 indicated by the area of detail 10.
Figure 13:
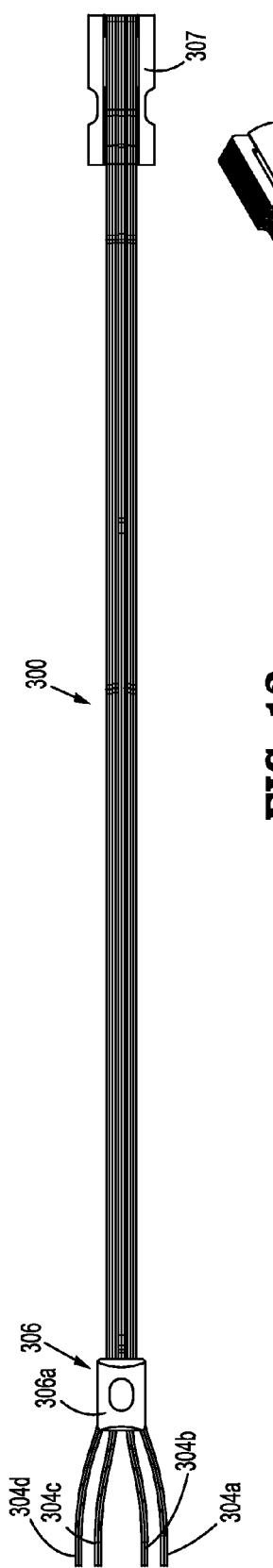
FIG. 13 is a top down view of the firing cam assembly of the cartridge assembly of FIG. 11.

With reference now to FIGS. 4 and 8-10, each retention slot 230 of inner and outer halves 226 and 228 of staple cartridge 208 has a staple magazine 244 operatively associated therewith. Each staple magazine 244 includes a recess 248 defined within the staple cartridges 206, 208, a plurality of staples 110 and a biasing member 246. The biasing member 246 is positioned to bias and urge the plurality of staples 110 towards a respective retention slot 230. As discussed above, the retention slots 230 are aligned in three different rows 234, 236 and 238 along the staple cartridges 206, 208. As discussed above, each row of retention slots 230 may receive different size staples 110. However, the staples 110 in each staple magazine 244 should be the same size. Referring now to FIG. 10, the recess 248 of the staple magazine 244 generally defines a "U" or "H" shaped channel 248 for reception of staples 110 therein. Channel 248 includes a pair of vertical segments 248a, 248b and a horizontal segment 248c. With reference to FIG. 5, each staple 110 disposed within channel 248 is maintained in a vertical orientation, with tips 110d oriented toward the tissue contacting surface 104 of the respective cartridge 206, 208. In this position, the backspan 110e of each of the staples 110 of each magazine 244 rests on horizontal segment 248c of channel 248 and the legs 112 of the staples 110 are disposed within the vertical segments 248a and 248b. The configuration of the channel 248 ensures that when a staple 110 is loaded from a magazine 244 into a respective retention slot 230, the staple 110 is properly the tissue contacting surface 104 for firing.

Each staple magazine 244 also defines a channel 244a which receives a portion of the biasing member 246 to secure the biasing member 246 in relation to the plurality of staples 110 of the staple magazine 244. Each biasing member 246 is configured to extend from the channel 244a into at least one of the vertical segments 248a and 248b of channel 248 which supports the plurality of staples 110 of each magazine 244. The biasing member 246 engages the plurality of staples 110 and urges the plurality of staples 110 towards the respective retention slot 230. It is contemplated that a separate biasing member 246 may extend into each vertical segment 248a and 248b. In the illustrated embodiment (FIG. 10), biasing member 246 includes a pair of legs 246b, 246c, and a backspan 246d. The pair of legs 246b, 246c extends into vertical segments 248a, 248b of the channel 248 when the biasing member 246 is inserted into channel 244a of magazine 244.

With reference again to FIGS. 4 and 10, when the legs 246b and 246c of the biasing member 246 are inserted through channel 244a into engagement with the plurality of staples 110, the legs 246b and 246c are deformed outwardly to bias the plurality of staples 110 to a position in vertical registration with the respective retention slot 230. The biasing member 246 is inserted into channel 244a in a substantially vertical manner and may be formed of any resilient or flexible material such as spring steel.

Alternately, the biasing member 246 may include any suitable mechanism for biasing the plurality of staples 110 disposed in each magazine 244 toward a respective retention slot 230, as described above, including, for example, springs, resilient members, or other similar biasing elements. Although illustrated as a leaf spring 246a having a substantially "U" shape, it is contemplated that the biasing member 246 may have other shapes suitable for use in biasing the staples 110 disposed in magazine 244 toward a retention slot 230.

With reference now to FIGS. 4, 5 and 9, a plurality of pushers 108 are disposed within each of the inner and outer halves 226, 228 of cartridges 206, 208. Each pusher 108 includes a pusher plate 108c which is slidably positioned within a respective retention slot 230 and is in engagement with a staple of the plurality of staples 110 of a staple magazine. Each pusher plate 108c is configured to translate through the respective retention slot 230 to urge a staple 110 disposed the retention slot 230 through a respective opening 230a in the tissue contacting surface 104, through tissue disposed between anvil assembly 22 and the cartridge assembly 20, and against staple forming pockets 22a (FIG. 18) of anvil assembly 22.

In one embodiment, as illustrated in FIG. 4, pusher plates 108c disposed in the retention slots 230 of first row 234 may have a first size, pusher plates 108c disposed in the retention slots 230 of second row 236 may have a second size, and pusher plates 108c disposed in retention slots 230 of third row 238 may have a third size. For example, pusher plates 108c of the first row 234 may be smaller than pusher plates 108c of second row 236, and pusher plates 108c of second row 236 may be smaller than pusher plates 108c of third row 238. Providing pusher plates 108c of different sizes allows pusher plates 108c to accommodate staples 110a-110c having different sizes and/or allows the pusher plates 108c to accommodate the different heights associated with the tissue contacting surfaces 104a-c associated with the rows 234, 236 and 238 of retention slots 230. Pusher plates 108c of each pusher 108 may alternatively be the same size. A tray or other member may be provided to maintain the position of the pushers prior to the staple cartridge being installed in the cartridge support channel.

Referring also to FIG. 5, each pusher 108 may be associated with one or more retention slots 230 such that upon actuation thereof, pusher 108 may fire one or more staples 110 from one or more rows of retention slots 230 through openings 230a. For example, a pusher 108a includes two pusher plates 108c and is configured to simultaneously fire two staples 110 from two adjacent rows of retention slots 230. As illustrated in FIG. 9, cartridge halves 226, 228 may include more than one type of pusher where, for example, pushers 108a, including two pusher plates 108c, that are configured for operative association with two retention slots 230 may be disposed at either end of the respective row 234, 236, 238, and pushers 108b, including three pusher plates 108c, that are configured for operative association with three retention slots 230 in two adjacent rows of retention slots 230 may be disposed between the ends of the respective rows 234, 236, 238. It is contemplated that alternate arrangements are possible where two and three retention slot pushers 108a, 108b may be included in any order. Alternatively, only one type of pusher 108 may be used, e.g., only pushers 108a configured for use with two retention slots or only pushers 108b configured for use with three retention slots. In this manner, each retention slot 230 is operatively associated with a pusher 108 that is configured to fire a fastener 110 disposed therein. It is alternatively contemplated that each pusher 108 may only include one pusher plate 108c and may only be associated with a single retention slot 230 or that each pusher 108 may include a plurality of pusher plates 108c configured for use with a plurality of retention slots 230.

Referring now to FIGS. 11-19, a firing cam assembly 300 is disposed at least partially within proximal housing 100 of loading unit 16 and extends into tool assembly 18. Firing cam assembly 300 is disposed in operative communication with handle assembly 12 and is configured to translate distally and proximally through tool assembly 18 upon actuation of handle assembly 12, as will be described below in more detail.

Figure 4A:
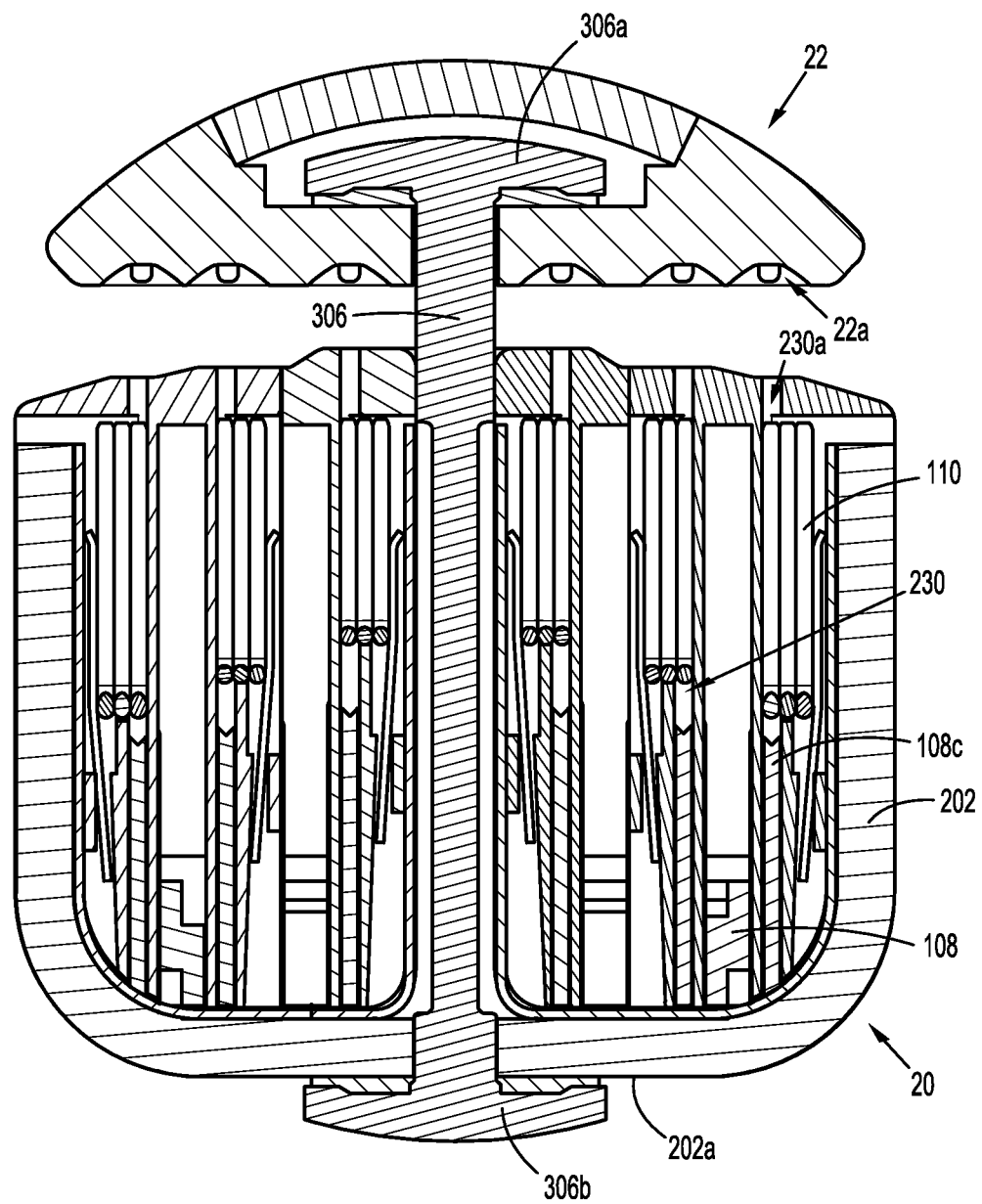
FIG. 4a is a cross-sectional view of the disposable loading unit of FIG. 3 taken along section line 4-4, illustrating the knife assembly disposed in the central channel and an anvil assembly.

With reference now to FIGS. 11-15, firing cam assembly 300 includes a plurality of drive bars 302 having firing cams 304a-d disposed at a distal end thereof and a central drive member 306 having a knife assembly 308 disposed at a distal end thereof. Knife assembly 308 defines a substantially I-shaped cross section having a top flange 306a, a bottom flange 308b and a knife blade 308c. As discussed above, a central longitudinal slot 252 defined between the staple cartridges 206, 208 extends along the length of cartridge assembly 20 to facilitate passage of central drive member 306 and knife assembly 308. With reference now to FIG. 4A, top flange 308a is configured to translate through a longitudinal slot 22b of anvil assembly 22 and bottom flange 308b is configured to translate longitudinally along an underside 202a of carrier 202.

Each half 226, 228 of each cartridge 206, 208 (FIGS. 11 and 12) includes a longitudinal slot 250 extending at least partially therethrough to accommodate passage of one of drive bars 302 and firing cams 304a-d of firing cam assembly 300 therethrough. It is contemplated, for example, that each slot 250 may accommodate passage of a single drive bar 302 and firing cam 304 or may accommodate passage of multiple drive bars 302 and firing cams 304.

With reference also to FIG. 4A, during operation of surgical stapling apparatus 10, as firing cam assembly 300 translates through loading unit 16, knife assembly 308 translates through longitudinal slot 250 with top flange 306a translating through longitudinal slot 22a of anvil assembly 22 and bottom flange 306b translating along underside 202a of carrier 202 to approximate anvil assembly 22 and cartridge assembly 20 together. As knife assembly 308 translates through slot 250, knife blade 308c severs the portion of tissue that is disposed between anvil assembly 22 and cartridge assembly 20 adjacent slot 250.

With reference also to FIGS. 16-19, as firing cam assembly 300 translates through the loading unit 16, drive bars 302 of firing cam assembly 300 translate through the longitudinal slots 250 of each half 226, 228 of each staple cartridge 206, 208. The firing cams 304 are advanced into sequential contact with the pushers 108 associated with retention slots 230, to cause pusher plates 108c to translate vertically within retention slots 230 and urge staples 110 from retention slots 230 through openings 230a in tissue contacting surface 104, through tissue disposed between anvil assembly 22 and the cartridge assembly 20, and against staple forming pockets 22a of anvil assembly 22 for staple forming.

Figure 19:
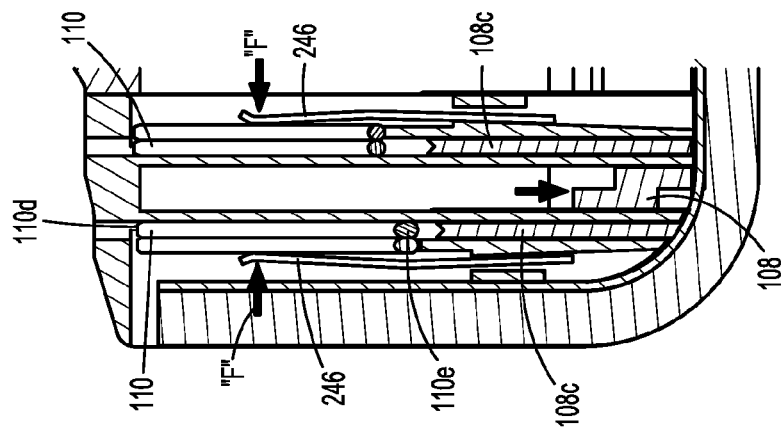
FIGS. 17-19 are enlarged cross-sectional views of the cartridge assembly of FIG. 4 indicated by the areas of detail 17, 18, 19 in FIG. 4, illustrating the firing and re-loading of a retention slot.
Figure 18:
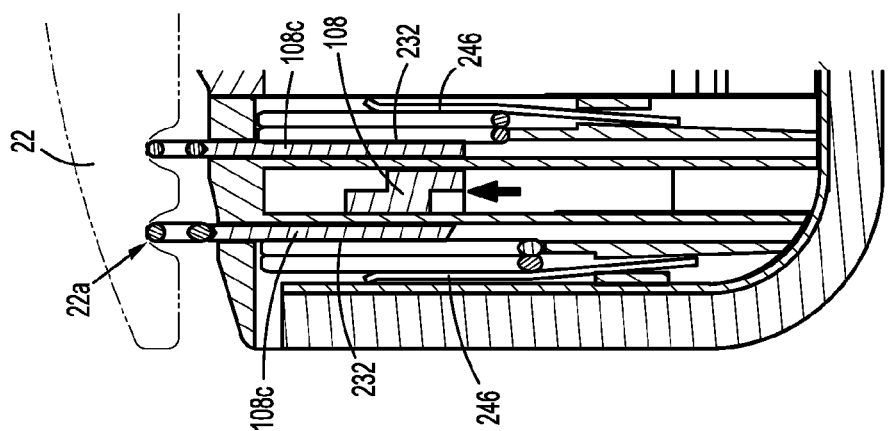
Figure 17:
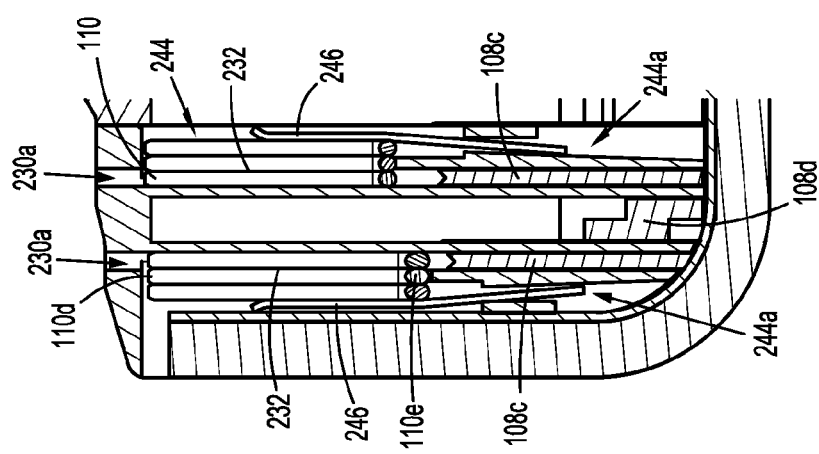

Referring now to FIGS. 17-19, during firing, as a pusher plate 108c translates through a corresponding retention slot 230 to a fired position, pusher plate 108c at least partially blocks or covers an opening 232 between retention slot 230 and magazine 244 to inhibit reloading of retention slot 230 with a new fastener 110 by magazine 244 until the firing stroke is complete. As pusher plate 108c returns to its pre-fired position at the base of retention slot 230, opening 232 is uncovered or opened to magazine 244 and receives the next staple 110 from magazine 244 due to biasing force "F" of biasing member 246. It is contemplated that the next staple 110 from magazine 244 may be at least partially received through opening 232 and within retention slot 230 as pusher plate 108c returns toward its pre-fired position where, for example, tips 110d of the next staple 110 may be received through opening 232 and within retention slot 230 before backspan 110e is received through opening 232 and within retention slot 230.

As illustrated, the drive bars 302a-d are initially disposed adjacent to one another within proximal housing 100 of the loading unit 16. However, each of the drive bars 302a-d is formed of a resilient, flexible material, e.g., spring steel and must facilitate translation through longitudinal slots 250.

Referring again to FIGS. 11-16, the firing cam assembly 300 may include, for example, four pairs of drive bars 302a-302d including four pairs of corresponding firing cams 304a-304d. Each pair of drive bars 302a-302d corresponds to a respective longitudinal slot 250a-250d of cartridges 206, 208 and is translatable through a respective longitudinal slot 250a-250d to actuate pushers 108 disposed in the respective longitudinal slot 250a-250d to effect firing of staples 110 disposed in corresponding retention slots 230. Drive bars 302a-302d and central drive member 306 are coupled together at their proximal end by welding or the like. The coupling member 307 is supported in a cutout formed in the proximal end of the firing cam assembly 300 and is configured to releasably engage a control rod 15 (FIG. 2) of the stapling apparatus 10.

Figure 16:
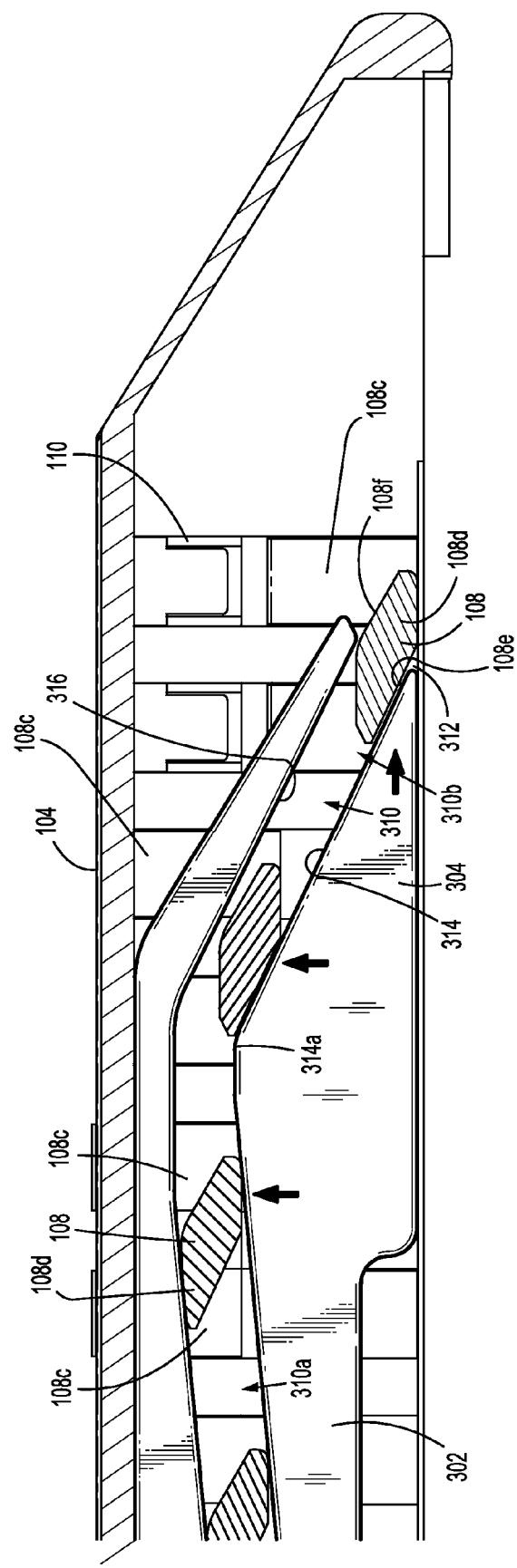
FIG. 16 is a side, cross-sectional view of the cartridge assembly of FIG. 6, taken along section line 16-16.

Referring to FIGS. 5 and 16, each pusher 108 includes a pusher base 108d having a proximal cam surface 108e and a distal cam surface 108f. Each pusher base 108d is disposed within one of longitudinal slots 250 with the proximal and distal cam surfaces 108e, 108f being configured for engagement with at least one of firing cams 304 upon distal translation thereof to cause pusher 108 to translate toward tissue contacting surface 104. Translation of pusher 108 in turn causes translation of a corresponding pusher plate 108c through a corresponding retention slot 230 toward tissue contacting surface 104 to eject staples 110 from the corresponding retention slots 230.

Referring now to FIGS. 14-19, each drive bar 302a-d and firing cam 304a-d includes a camming slot 310 having a proximal portion 310a and a distal portion 310b. Distal portion 310b includes an opening 312, a firing cam surface 314 and a retracting cam surface 316. Opening 312 is configured to receive the pusher base 108d such that the proximal cam surface 108e of pusher base 108d engages firing cam surface 314 during distal translation of the firing cam 304. Each firing cam surface 314 is sloped such that as proximal cam surface 108e of pusher base 108d slides along firing cam surface 314, pusher 108 is urged toward tissue contacting surface 104 from a pre-fired position to a fired position. As pusher 108 is urged toward tissue contacting surface 104, the corresponding pusher plate 108c translates through the corresponding retention slot 230 to drive the staple 110 disposed in the retention slot 230 through opening 230a of tissue contacting surface 104, through tissue disposed between anvil assembly 22 and cartridge assembly 20, and against a staple forming pocket 22a of anvil assembly 22.

Once the pusher base 108d reaches the fired position at a top portion 314a of firing cam surface 314, drive bars 302a-d and firing cams 304a-d are further translated distally such that pusher base 108d slides along camming slot 310 towards proximal portion 310a. Proximal portion 310a of camming slot 310 is dimensioned such that as drive bars 302a-d and firing cams 304a-d continue to translate distally, pusher base 108d remains in the fired position. This allows the corresponding pusher plate 108c to remain in a position which at least partially blocks or covers the opening 232 of retention slot 230 (FIG. 18) to inhibit loading of the next staple 110 from the corresponding magazine 244 associated with the respective retention slot 230. Camming slot 310 extends a sufficient distance along drive bar 302 to accommodate a full firing stroke of firing cam assembly 300 where, for example, when drive bars 302a-d and firing cams 304a-d are in a distal most position, a proximal end 310c of camming slot 310 is disposed adjacent to or proximal of the proximal most pusher 108.

During refraction of firing cam assembly 300 after the firing stroke, the distal cam surfaces 108f of pushers 108 are engaged by retracting cam surface 316 of drive bars 302a-d as drive bars 302a-d and firing cams 304a-d are translated proximally. The distal cam surfaces 108f or pushers 108 are driven along retracting cam surface 316 of drive bars 302a-d toward opening 312 of camming slot 310 to return the pusher 108 from the fired position to the pre-fired position. As each pusher 108 slides along retracting cam surface 316 of firing cam 304 toward the pre-fired position, the corresponding pusher plate 108c translates toward a base of the corresponding retention slot 230 and opens up or uncovers the opening 232 of the corresponding retention slot 230 to the corresponding magazine 244. Once opening 232 is uncovered, retention slot 230 receives the next staple 110 from the magazine 244 due to the biasing force of biasing member 246. When the firing cam assembly 300 is fully retracted and each retention slot 230 has been loaded with a new staple 110 from a corresponding magazine 244, the surgical stapling apparatus 10 is ready to perform a stapling and cutting operation.

Referring now to FIGS. 4-10 the assembly of cartridge assembly 20 will now be described. A staple pusher 108 is positioned in operative association with each retention slot 230 with pusher base 108d being disposed in one of longitudinal slots 250 of each half 226, 228 of each cartridge 206, 208. Staples 110 are loaded into retention slots 230 through the "U" or "H" shaped channels 248 and the biasing members 246 are inserted into the channels 244a of the magazines 244 such that legs 246b, 246c extend into the vertical segments 248a, 248b of channels 248 and bias the staples 110 of a respective staple magazine 244 toward retention slots 230.

Once the components of each half 226, 228 of each cartridge 206, 208 have been assembled, inner and outer halves 226, 228 of each cartridge 206, 208 are joined or coupled together by positioning the flanges 240 of each half 226, 228 and into the channels 242 of each other half 226, 228 to interlock the halves 226, 228 together. The assembled inner and outer halves 226, 228 are then inserted into the cartridge support channel 254 which maintains inner and outer halves 226 and 228 in engagement with one another.

Referring now to FIGS. 6 and 7, the assembled cartridges 206, 208 are joined together at the distal end portion 216 by positioning the inner tab 224 within the inner hole 222 so as to define the central longitudinal slot 252. The joined cartridges 206, 208 are inserted into elongated support channel 204 of carrier 202 such that tabs 210 disposed on cartridges 206, 208 are positioned within the slots 212 of carrier 202 and support struts 214 of cartridges 206, 208 rest on the side walls of carrier 202. The cartridge assembly 20 is now assembled and ready for use.

The operation of surgical stapling device 10 during a surgical procedure will now be discussed with reference to FIGS. 16-19. During the surgical procedure, the surgeon attaches the loading unit 16 to the elongated body 14 (FIG. 1) and inserts the loading unit 16 into the surgical site through an incision and/or cannula. The surgeon manipulates the stapling apparatus 10 to position tissue between cartridge assembly 20 and anvil assembly 22 and actuates handle assembly 12 to approximate the anvil assembly 22 with the cartridge assembly 20 and grasp the tissue. After confirming that the desired tissue is positioned between the anvil assembly 22 and the cartridge assembly 20, the surgeon actuates handle assembly 12 to drive firing cam assembly 300 distally through cartridge assembly 20 and fire the surgical staples. It is contemplated that a single actuation of handle assembly 12 by the surgeon may grasp tissue and fully fire the surgical stapling device 10. Alternatively, grasping tissue and firing of the surgical stapling device may require multiple actuations of handle assembly 12 with each actuation advancing firing cam assembly 300 a predetermined distance through loading unit 16. It is contemplated that the handle portion can be a motorized handle assembly or robotically controlled actuator. Such motorized handle assembly or robotically controlled actuator can include a controller and/or power source.

As firing cam assembly 300 translates through cartridge assembly 20, each pair of drive bars 302a-302d and attached pairs of firing cams 304a-304d translate through respective longitudinal slots 250 of one of inner and outer halves 226, 228, of cartridges 206, 208. During distal translation of firing cams 304a-304d, each firing cam 304 engages a series of pusher 108 to sequentially drive the pushers 108 toward the tissue engaging surface 104 of the cartridge assembly 20 and eject staples 110 from the retention slots 230 disposed in cartridges 206, 208.

As discussed above, as each firing cam 304 engages a pusher 108, the proximal cam surface 108e of the pusher 108 engages the firing cam surface 314 of the firing cam 304 and is driven up the firing cam surface 314 from the pre-fired position to the fired position, e.g., towards tissue contacting surface 104. As the pusher 108 is driven towards tissue contacting surface 104, its respective pusher plate 108c translates through a corresponding retention slot 230 to eject a corresponding staple 110 from the corresponding retention slots 230 through a respective opening 230a in tissue contacting surface 104, through tissue disposed between anvil assembly 22 and cartridge assembly 20, and against staple forming pockets 22a of anvil assembly 22, thereby forming each staple 110. As the firing cam 304a-d continues to translate distally, pusher base 108d travels along camming slot 310 toward proximal end portion 310a and is maintained in a raised or fired position, e.g., driven toward tissue contacting surface 104, such that the corresponding pusher plate 108c blocks or covers the opening 232 between the retention slot 230 and the corresponding magazine 244. As firing cam assembly 300 translates distally, knife assembly 308 also translates distally through central longitudinal slot 252 to sever the tissue held between the cartridge assembly 20 and anvil assembly 22.

Once the firing stroke is complete, with firing cam assembly 300 disposed in a distal most position, the surgeon retracts the firing cam assembly 300, such as by withdrawing retraction member 34 (FIG. 1) proximally. As firing cam assembly 300 translates proximally through cartridge assembly 20, firing cams 304a-d are translated proximally through longitudinal slots 250 such that the distal cam surface 108f of each pusher base 108d engages the retracting cam surface 316 to drive the pusher base 108d down toward opening 312 and the pre-fired or lowered position. As each pusher base 108d is driven toward opening 312, each pusher is translated away from tissue contacting surface 104 and each pusher plate 108c is translated away from tissue contacting surface 104 toward the pre-fired position within a corresponding retention slot 230. As each pusher plate 108c is withdrawn to the pre-fired position, the opening 232 between the retention slot 230 and the corresponding magazine 244 is uncovered to allow the next staple 110 to be moved from the staple magazine 244 into a respective retention slot 230 due to the biasing force "F" (FIG. 19) of the corresponding biasing member 246. Once firing cam assembly 300 is fully translated proximally to a pre-firing position, each retention slot 230 has been reloaded and surgical stapling apparatus 10 is ready to perform a stapling and cutting procedure. In this manner, each retention slot 230 is reloaded in-situ and ready for subsequent use without requiring the surgeon to withdraw the loading unit 16 from the surgical site or replace the loading unit 16.

It is contemplated that each loading unit 16 may be configured for multiple firing strokes.

Figure 15:
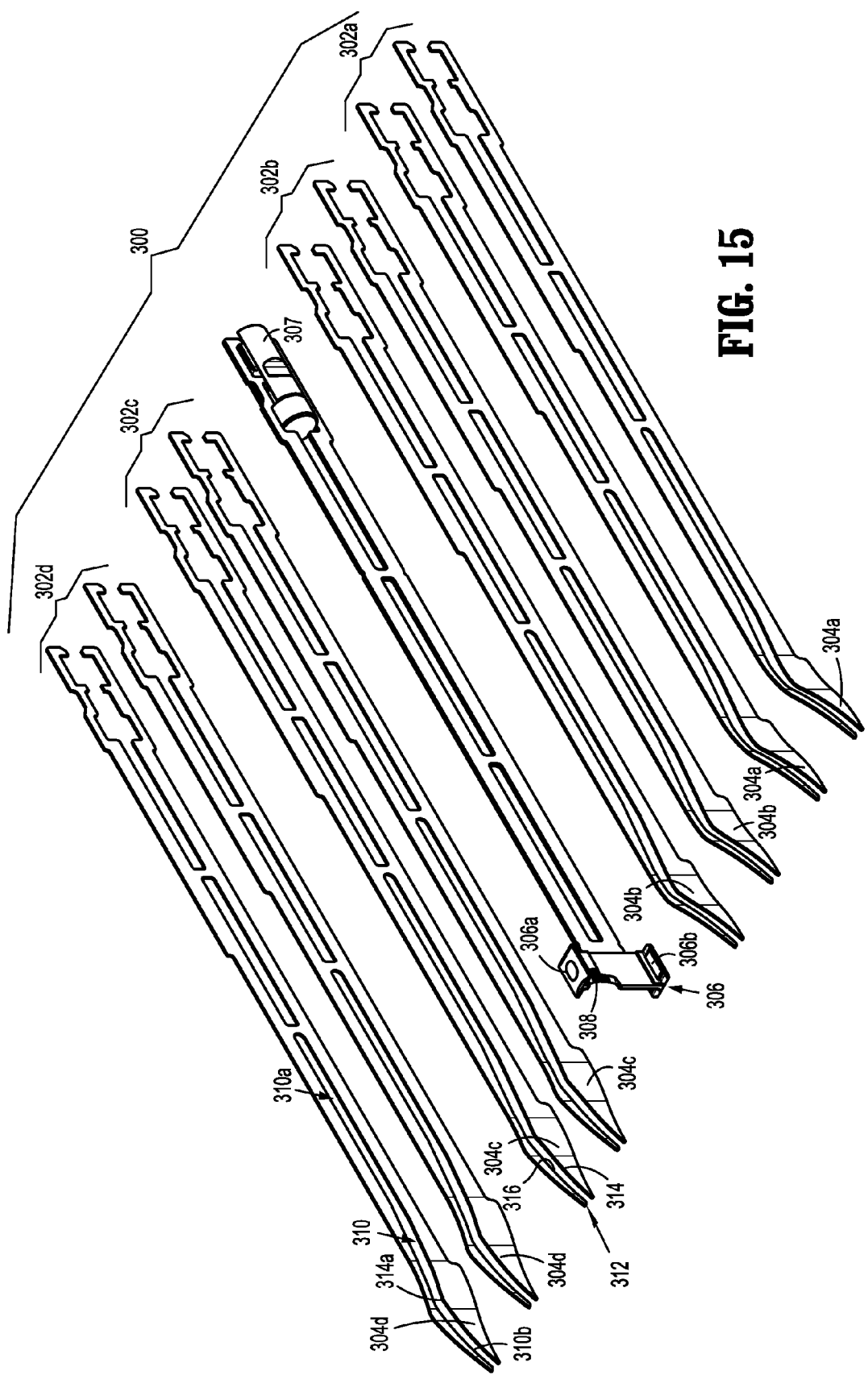
FIG. 15 is an exploded view of the firing cam assembly of FIG. 14.

In any of the embodiments disclosed herein, the drive bars 302 can be configured as more than one bar partially attached to each other. As shown in FIG. 15, each drive bar is comprised of two drive bars. Each bar can be attached, or partially attached, to at least one other adjacent bar, in any of the embodiments disclosed herein. They may be attached by adhesives or welding. For example, a drive bar comprised of two bars is welded together at the distal end, near the cam surface. Each staple pusher is driven by a pair of such cam bar assemblies, as described in [0083]-[0086]. The assembly has better flexibility and permits articulation. Welding two or more bars together gives the bar assembly more stiffness and is desirably welded near the cam surface 304. In any of the embodiments disclosed herein, a pair of relatively thinner bars is used, instead of a single relatively thicker bar, which is at least partially attached to one another.

FIGS. 20-31 illustrate an alternate embodiment of a tool assembly shown generally as 418 for use with surgical stapling apparatus 10 (FIG. 1). The tool assembly 418 includes a cartridge assembly 420 and an anvil assembly 422. The anvil assembly 422 is substantially as described above with respect to anvil assembly 22 (FIG. 1) and will not be described in further detail below. The cartridge assembly is provided to effect multiple staple firings and to lockout the cartridge assembly 420 when depleted of staples.

Figures 22, 22A:
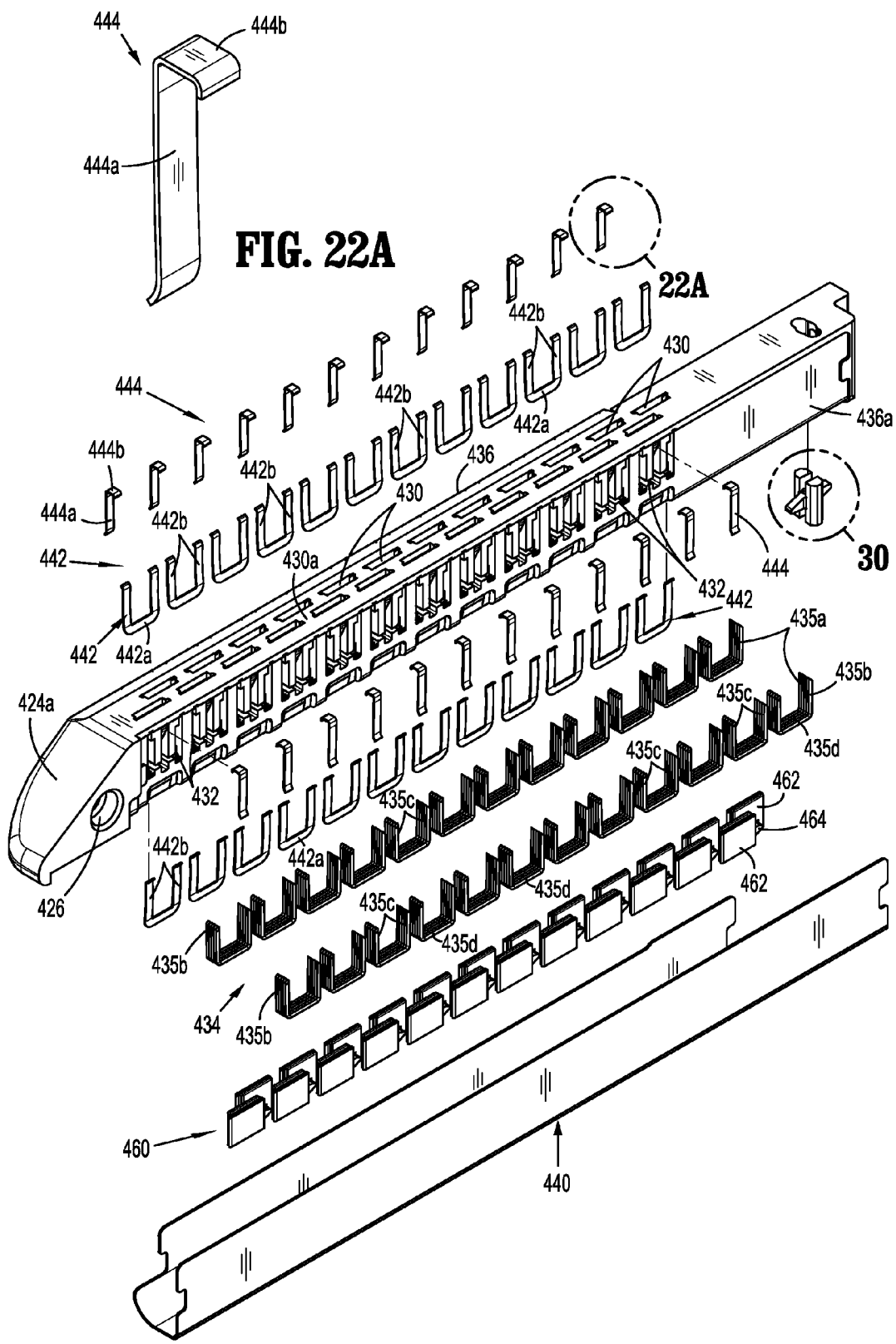
FIG. 22 is an exploded, side perspective view of one half of the cartridge body shown in FIG. 20.
FIG. 22A is a first side perspective view of a second biasing member of the cartridge assembly shown in FIG. 22.
Figure 23:
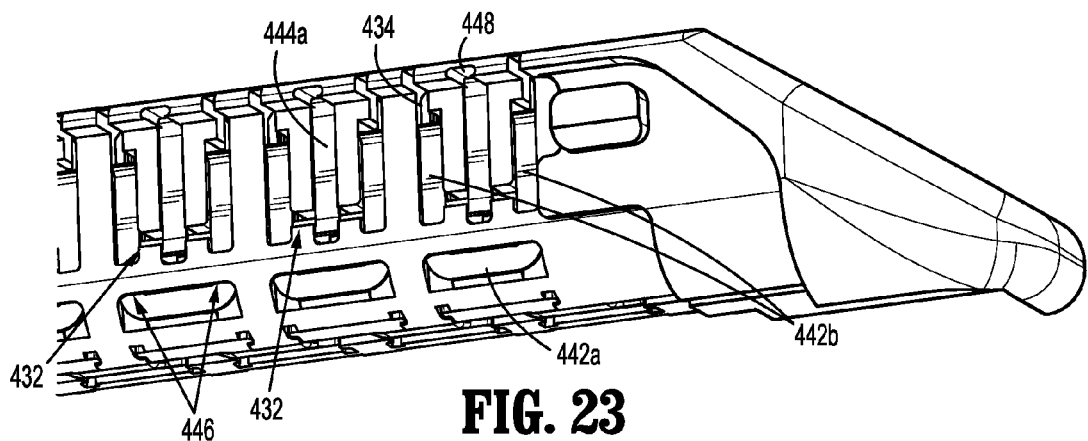
FIG. 23 is a side perspective view of the cartridge body half shown in FIG. 21 with a cartridge support channel removed.
Figure 24:
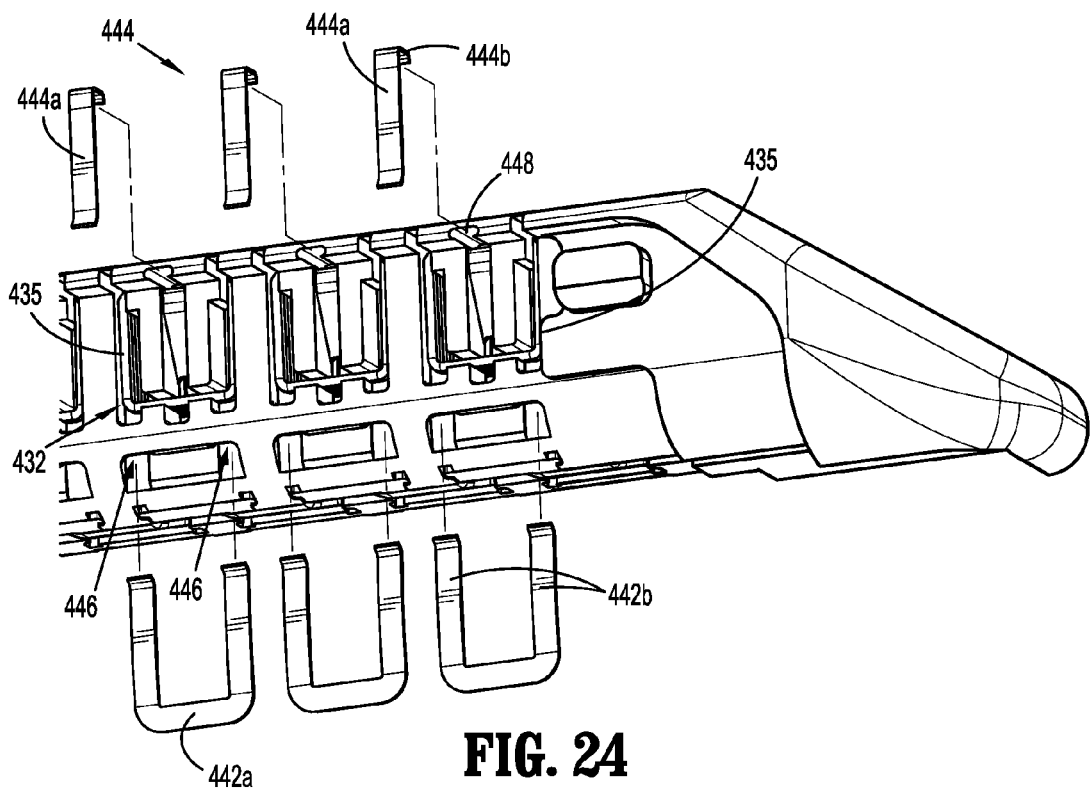
FIG. 24 is a side perspective view of the cartridge body half shown in FIG. 23 with the first and second biasing members separated from the cartridge body half.
Figure 25:
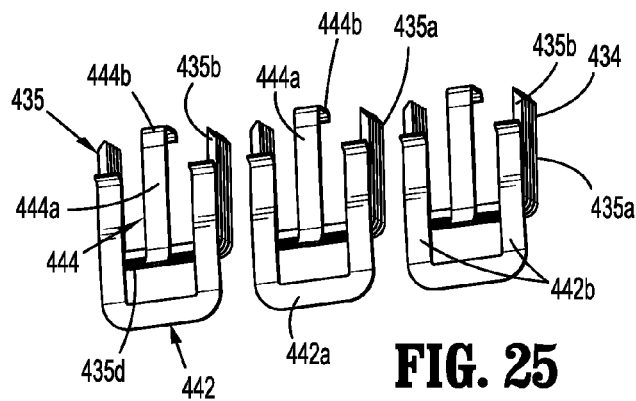
FIG. 25 is a side perspective view of the staple magazine shown in FIG. 22 in association with the first and second biasing members.

Referring to FIGS. 20-22, the cartridge assembly 420 includes a first body half 424a, a second body half 424b, a pair of cartridge half support channels 440 for supporting each of first and second body halves 424a and 424b, and a carrier 202 (FIG. 20A) defining a channel for receiving the support channels 440. The first body half 424a defines a distally located hole 426 and the second body half 424b defines distally located tab or a protrusion 428. The tab 428 is positioned within the hole 426 to axially fix the distal end of the first body half 424a in relation to the second body half 424b. Alternately, other fastening techniques on devices can be used to secure the first and second body halves together. When the first and second body halves 424a and 424b are fixed together, the body halves 424a and 424b define a knife channel 427 (FIG. 20).

Each body half 424a and 424b defines a plurality of retention slots 430 which are aligned in two linear rows. The retention slots 430 open onto a tissue contact surface 430a of a respective body half 424a, 424b. Alternatively, additional rows of retention slots 430 may be provided in each body half 424a, 424b.

Referring to FIGS. 22-27, body half 424a is a mirror image of body half 424b. As such, only body half 424a will be described in further detail herein. Body half 424a defines a plurality of recesses 432 which open onto inner and outer sidewalls 436a and 436b, respectively of body half 424b. Each recess 432 of the plurality of recesses 432 communicates with a retention slot 430 and houses a magazine 434 of staples 435 including a staple 435a aligned with a retention slot 430. Although each magazine 434 of staples 435 is illustrated to include five staples 435, it is envisioned that each magazine 434 of staples 435 can include a different number of staples 435, e.g., 2 or more. The recesses 432 are in lateral alignment with a respective retention slot 430. Each recess 432 defines a U-shaped track which allows the magazine 434 of staples 435 to slide toward the retention slot 430 as the staples 435 are ejected. The end of each recess 432 adjacent each sidewall 436 is enclosed by the cartridge support channel 440 which retains each staple magazine 434 within its respective recess 432.

Body half 424a supports a plurality of first biasing members 442 and a plurality of second biasing members 444. One first biasing member 442 and one second biasing member 444 is associated with each recess 432 and each staple magazine 434. The first biasing member 442 is similar to biasing member 246 described above and includes a U-shaped resilient member having a backspan 442a and a pair of legs 442b. The legs 442b of each of the first biasing members 442 extend through openings 446 (FIG. 24) and into the recess 432. When inserted through the openings 446, the legs 442b are positioned to engage the legs 435c of the outermost staple 435b (FIG. 25) nearest a sidewall 436a, 436b to urge the staple magazine 434 inwardly towards a respective retention slot 430.

Each of the second biasing members 444 (FIG. 22A) includes a single resilient leg 444a and a connecting portion 444b which is configured to secure the second biasing member 444 within the body half 424a. The connecting portion 444b includes a transverse member 444b which is received within a cutout 448 (FIG. 26) formed in the body half 424a to secure the second biasing member 444 within a central portion of each recess 432. The second biasing member 444 is supported within the body half 424a such that the resilient leg 444a engages the backspan 435d of the staple 435b of the magazine 434.

Figure 26:
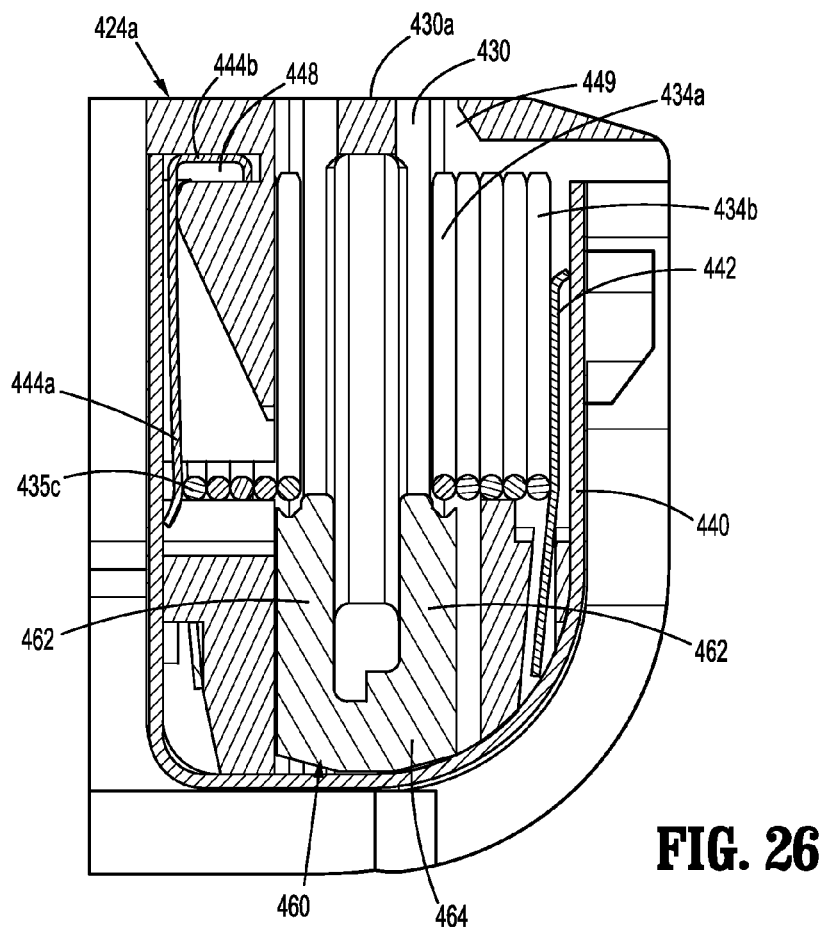
FIG. 26 is a cross-sectional view taken along section line 26-26 of FIG. 21 with a full staple magazine.
Figure 27:
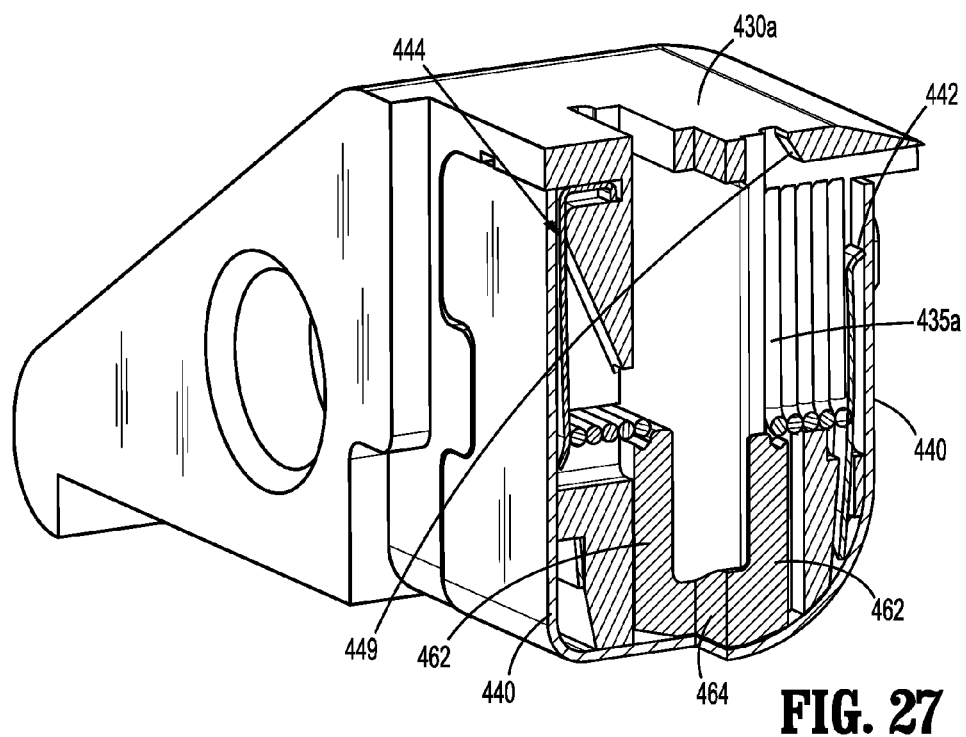
FIG. 27 is a side perspective, partial cross-sectional view of the cartridge body half shown in FIG. 26 with a full staple magazine.
Figure 28:
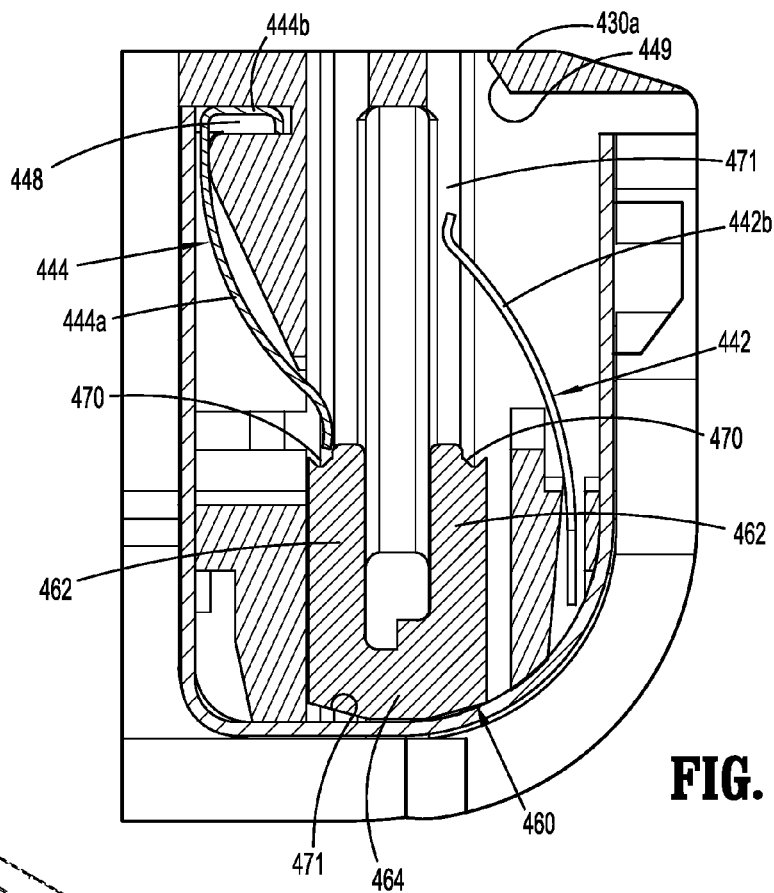
FIG. 28 is a cross-sectional view taken through the cartridge body half of FIG. 21 with a depleted staple magazine.
Figure 29:
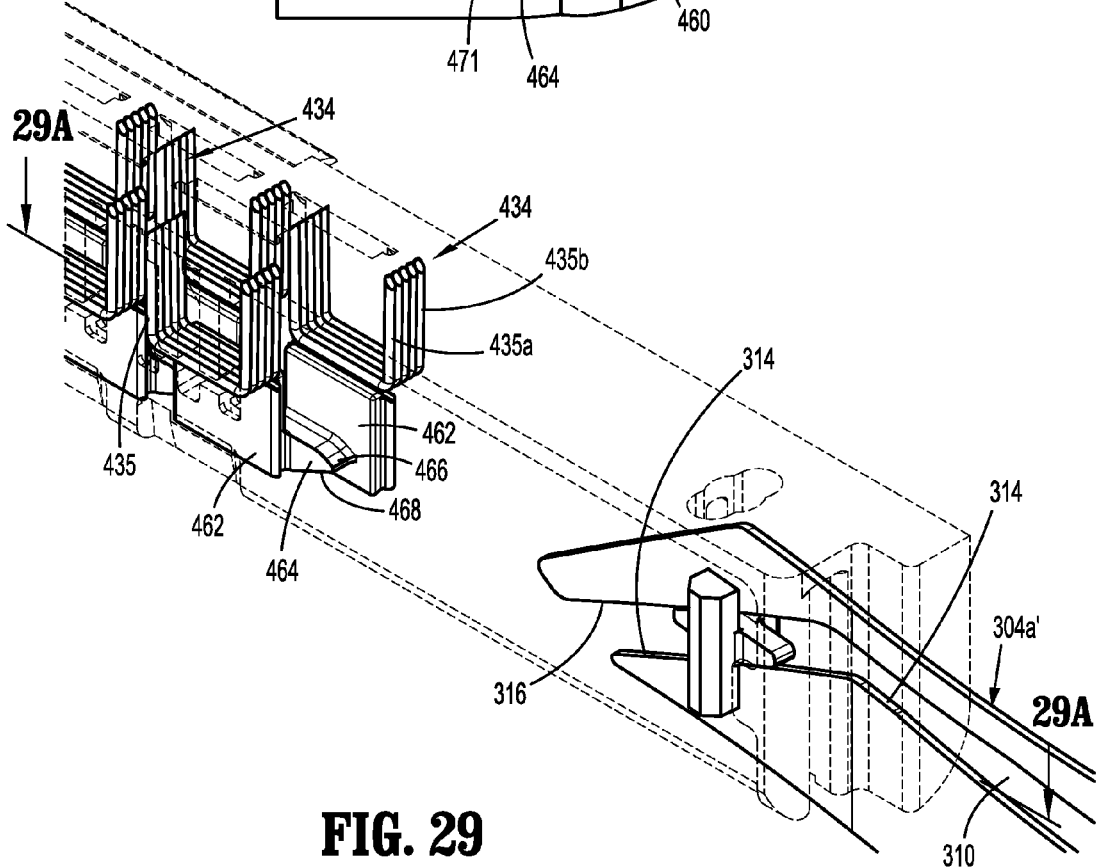
FIG. 29 is a side perspective view of the cartridge body half of the tool assembly shown in FIG. 1 with the cartridge body half shown in phantom, and a distal end of the firing cam assembly positioned proximally of the staple pushers.
Figure 30:
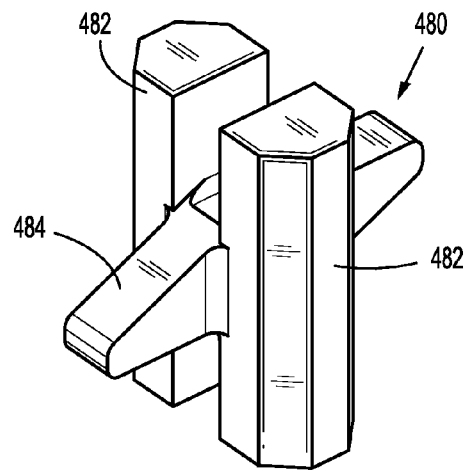
FIG. 30 is a side perspective view of a cam separation of a cartridge body half of the cartridge assembly shown in FIG. 22.

Referring to FIGS. 26-29B, the body half 424a supports a plurality of pushers 460. Each of the pushers 460 is substantially similar to pusher 108 described above (FIG. 5) and includes a pair of pusher plates 462 interconnected by a pusher base 464. The pusher base 464 defines an upper cam surface 466 and a lower cam surface 468 (FIG. 29). Each pusher plate 462 is slidably positioned in a respective retention slot 430 from a lower position to a raised or fired position to eject a staple 435 of the magazine 434 from a retention slot 430. As illustrated in FIG. 26, an inner tapered wall 449a of the body half 424a defines a lead-in chamber 449 to guide the staples 435a from the retention slots 430 through the tissue contact surface 430a.

Referring to FIG. 28, an upper surface of each pusher plate 462 defines a notch 470. When the last staple 435b of the staple magazine 434 is ejected from its respective retention slot 430 and the pusher 460 is returned to the lower position as will be discussed below, the resilient leg 444a of the second biasing member 444 springs into the retention slot 430 to obstruct movement of the pusher plate 462 within the retention slot 430 back to the raised position. More specifically, the leg 444a of the second biasing member 444 moves to a position aligned with the notch 470 to prevent movement of the pusher 460 back to the raised position as will be discussed in further detail below.

The tool assembly 418 includes a firing cam assembly similar to firing cam assembly 300 (FIGS. 14-16) as discussed above with respect to tool assembly 18. The firing cam assembly 300 for use with tool assembly 418 includes two firing cams 304a' (only one firing cam 304a' is shown). As illustrated in FIG. 29, each of the firing cams 304a' includes a first blade 314a and a second blade 316a which are separated by a camming slot 310. The camming slot 310 receives the pusher base 464 of a respective pusher 460 as the firing cam 304a' is moved within firing cam channel 471 (FIG. 28) to control movement of the pusher 460 between the lower position and the raised or fired position. More specifically, when the firing cam 304a' is translated distally through the firing cam channel 471 of the cartridge body half 424a, the pusher base 464 is received within and translates along camming slot 310 of firing cam 304a'. As this occurs, lower cam surface 468 (FIG. 29) of pusher base 464 rides up along firing cam surface 314 of the first blade 314a of the firing cam 304a' to move the pusher 460 from the lower position to the raised or fired position. Subsequently, when the firing cam 304a' is translated proximally within firing cam channel 471, the upper cam surface 466 of the pusher base 464 is engaged by a retracting cam surface 316 of the second blade 316a of the firing cam 304a' to return the pusher 460 to the lower position.

Referring again to FIGS. 29-31, the cartridge assembly 420 further includes a cam separator 480 associated with each firing cam 304a'. Each cam separator 480 (FIG. 30) includes a pair of guide members 482 which are interconnected by a cam member 484. The cam separator 480 is slidably positioned within a vertical channel 490 (FIG. 21) formed in the body halves 424a, 424b. As such, each cam separator 480 is axially fixed but vertically movable within the cartridge body half 424a, 424b. The cam separator 480 is positioned such that the cam member 484 is received within a distal end of the camming slot 310 of a respective firing cam 304a' (FIG. 29) of the firing cam assembly when the firing cam 304a' is in a retracted position. As the firing cam 304a' is moved from the retracted position to the advanced position, the cam separator 480 will be moved from a lower position to a raised position within the vertical channel 490 of the body halves 424a, 424b. The cam separator 480 maintains proper separation of the first and second blades 314a and 316a, of the firing cam 304a' prior to and during advancement of the firing cam 304a'.

Referring to FIG. 29, the tool assembly 418 functions in a manner substantially as described above with regard to tool assembly 18. More specifically, when the stapling device 10 (FIG. 10) is actuated to advance the firing cam 304a' by, for example, moving movable handle 26 towards stationary handle 26 in relation to stationary handle 24 (FIG. 1), the firing cam 304a' moves distally within cam channel 471 of body half 424a such that the pusher base 464 of pusher 460 is received within camming slot 310 of the firing cam 304a'. It is noted that the presently disclosed tool assembly is also suitable for use with motorized or robotically actuated surgical devices. As the firing cam 304a' moves distally in relation to each pusher 460, the firing cam surface 314 of firing cam 304a' is positioned beneath the pusher base 464 and urges the pusher base 464 and thus, the pusher 460, upwardly. As the pusher 460 moves upwardly, the pusher plates 462 move upwardly within the retention slots 430 to force a staple 435a of the staple magazine 434 upwardly and out of the retention slot 430. When the pusher 460 is in its raised or firing position, the pusher plates 462 block entry of the next staple 435 of the staple magazine 434 from entering the retention slot 430.

Figure 31:
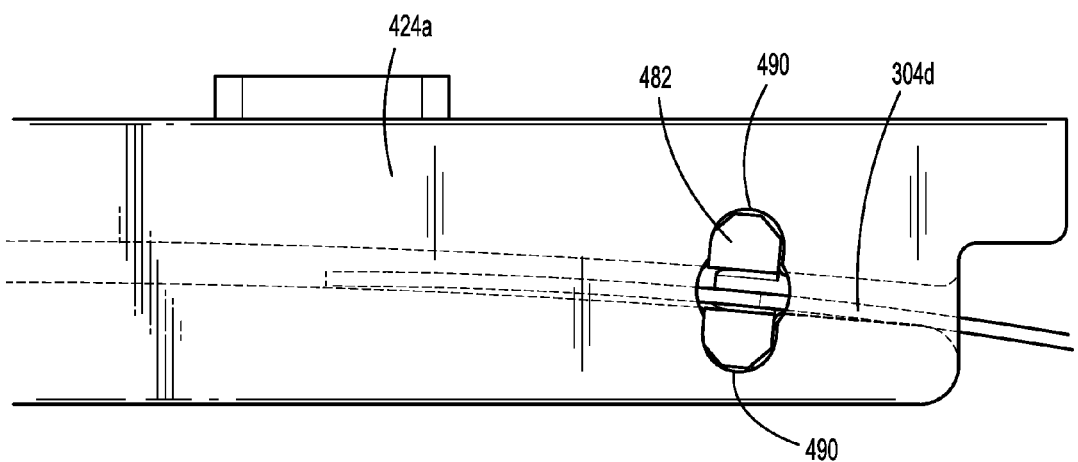
FIG. 31 is a schematic top view of a cartridge body half illustrating the cam separator and cam drive bar and the cam pathway in phantom.
Figure 32:
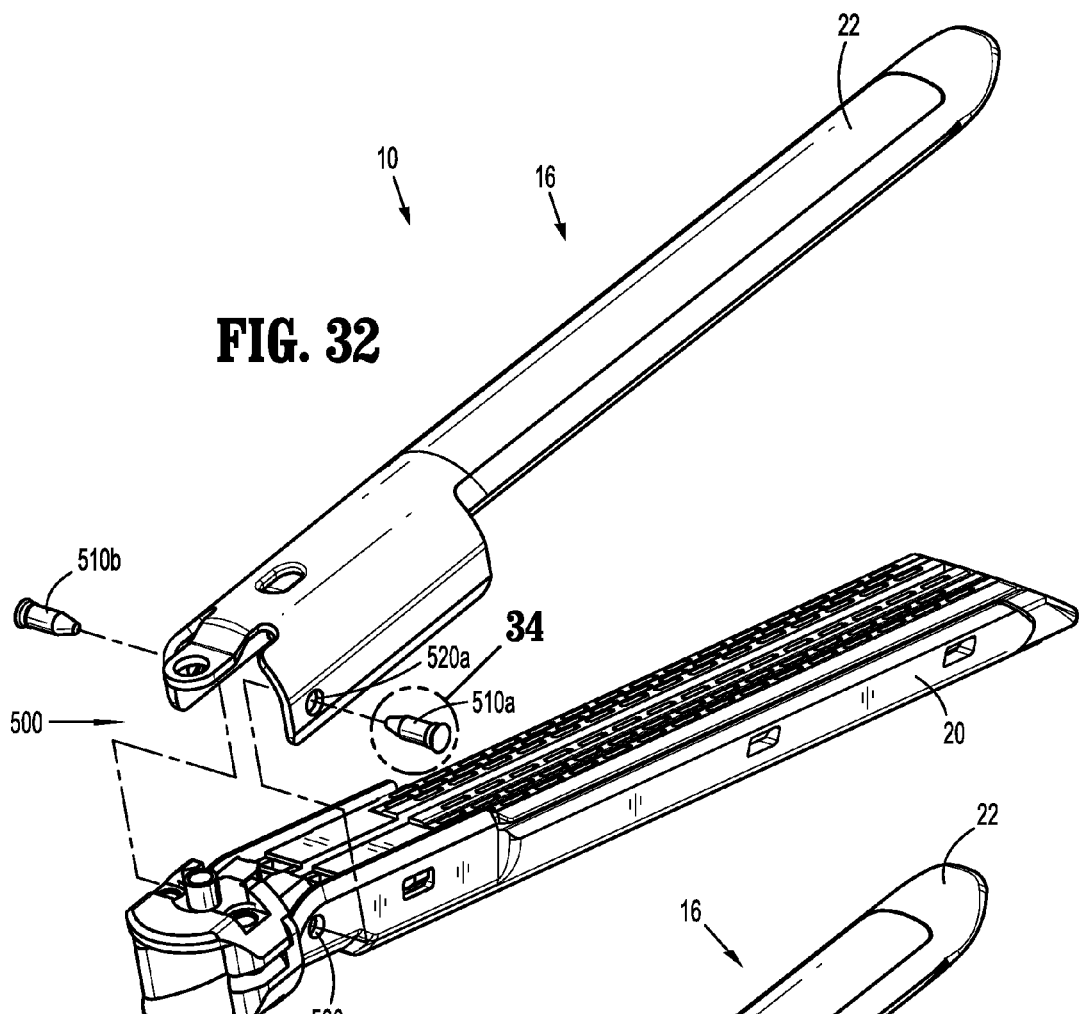
FIG. 32 is a perspective, assembly view of a loading unit including a pivot mechanism in accordance with embodiments of the present disclosure.
Figure 33:
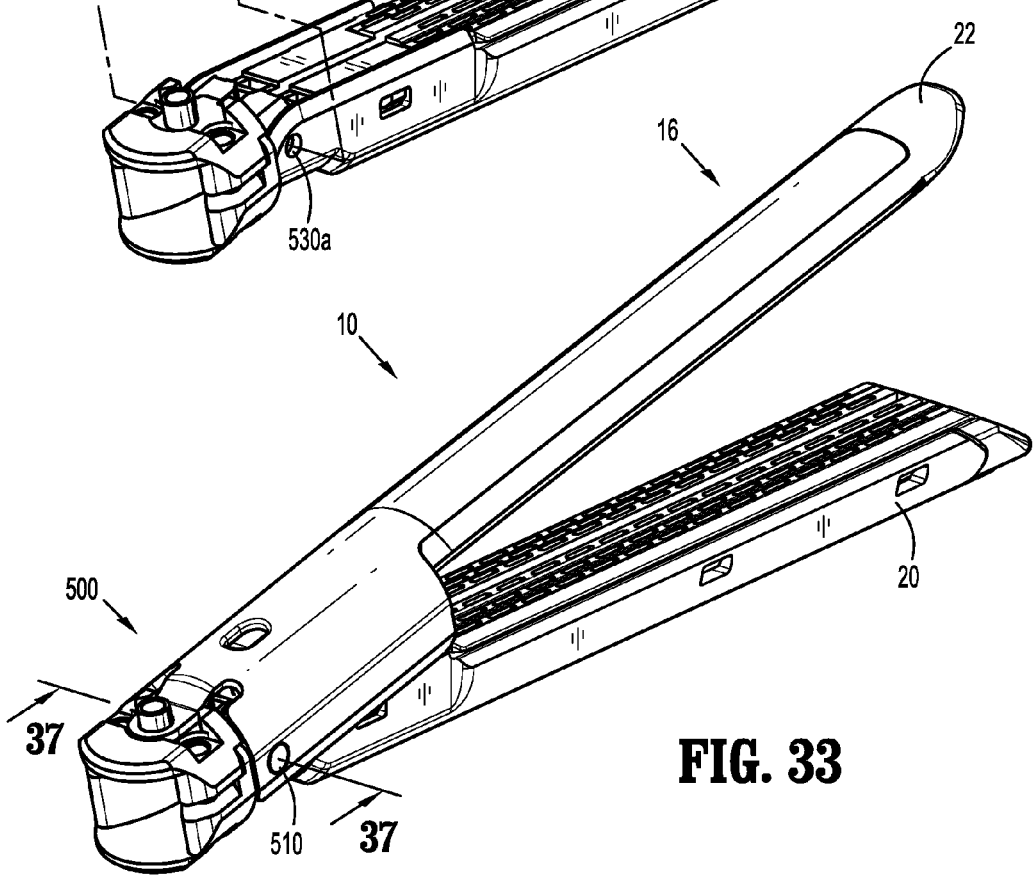
FIG. 33 is a perspective, assembled view of the loading unit including the pivot mechanism of FIG. 32.

When the firing cam 304a' is retracted within the firing cam channel 471, the pusher base 464 of each pusher 460 moves along camming slot 310 to move the pusher 460, and thus, the pusher plates 462, downwardly to the lower position. When the pusher plates 462 pass by recesses 432 (FIG. 27), the first and second biasing members 442 and 444 push the staple magazine 434 towards the retention slots 430 to place the next staple 435 of the staple magazine 434 into alignment with the retention slot 430. This process can be repeated to eject each of the staples 435 from the staple magazine 434. As shown in FIGS. 29 and 31, the cam separator 480 maintains proper spacing between the first blade 314a and the second blade 314b of the firing cam 304a' when the firing cam 304a' is in the retracted position.

Referring to FIG. 28, after the last staple 435b of each staple magazine 434 is ejected from the body half 424a, the resilient leg 444a of the second biasing member 444, which no longer engages a staple backspan 435d springs into a position above the notch 470 formed in each pusher plate 462 of the pusher 460 to prevent movement of the pusher 460 from the lower position back to the raised position. Since the pushers 460 are locked in the lower position, movement of the firing cam 304a' through the cartridge body half 424a is prevented and the tool assembly 418 is locked out.

Figure 14:
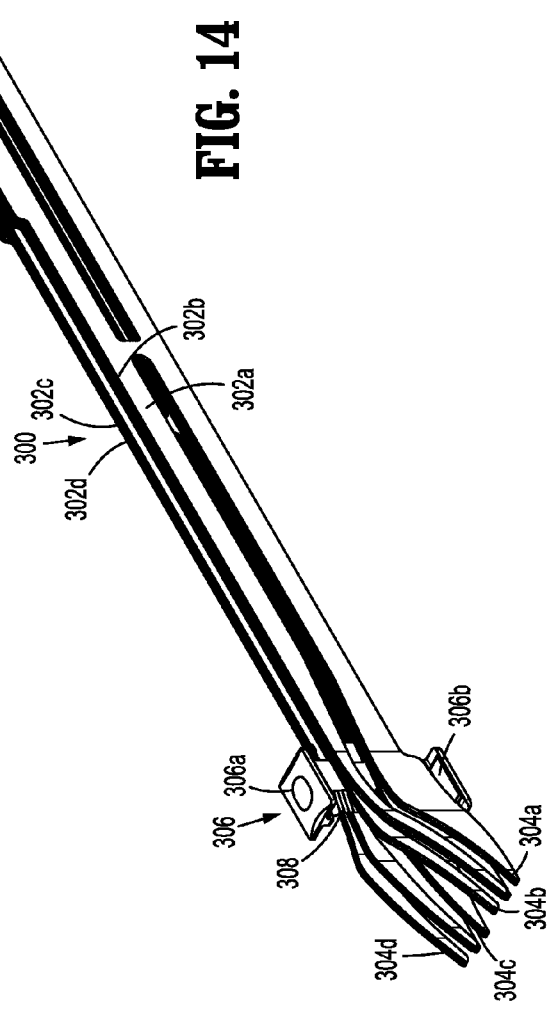
FIG. 14 is a perspective view of the firing cam assembly of FIG. 13.

As discussed above, the cartridge assembly 420 includes first and second cartridge body halves 424a and 424b. Cartridge body half 424b also includes a firing cam 304a'. Although not shown, the tool assembly 418 also includes a firing cam assembly such as shown in FIG. 14 which includes the firing cams 304a' (FIG. 29), a central drive member 306 and a knife 308. Alternatively, the cartridge assembly 420 may only have one or more rows of staples which are supported in a cartridge body as described above. The cartridge assembly need not include a knife.

With reference to FIGS. 32-43 a pivot mechanism 500 of surgical stapling device 10 is shown. Pivot mechanism 500 includes a first pivot pin 510a, a second pivot pin 510b, a first aperture 520a of anvil assembly 22, a second aperture 520b of anvil assembly 22, a first aperture 530a of cartridge assembly 20, and a second aperture 530b of cartridge assembly 20 (see FIG. 37). For ease of description, first pivot pin 510a and second pivot pin 510b are collectively referred to as pivot pin 510; first aperture 520a and second aperture 520b of anvil assembly 22 are collectively referred to as anvil aperture 520 or aperture 520; and first aperture 530a and second aperture 530b of cartridge assembly 20 are collectively referred to as cartridge aperture 530 or aperture 530.

Pivot mechanism 500 is configured to establish a secure, robust and accurate pivotal connection between cartridge assembly 20 and anvil assembly 22, while providing an arrangement that reduces the force to install pivot pins 510 into apertures 520, 530 in comparison to conventional pivot mechanisms.

Figure 34:
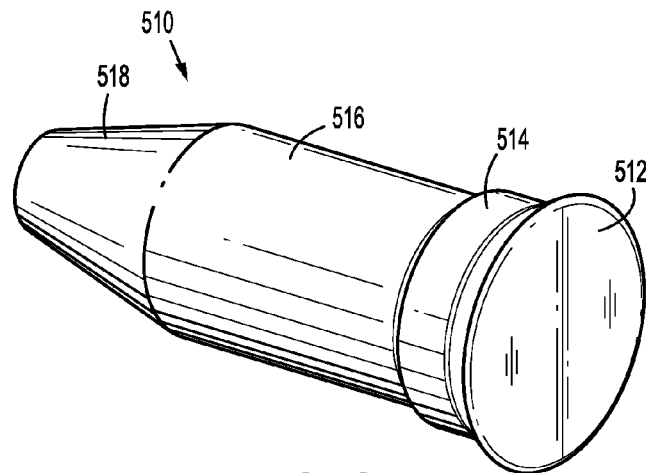
FIG. 34 is a rear perspective view of a pivot pin of the pivot mechanism indicated in FIG. 32.
Figure 35:
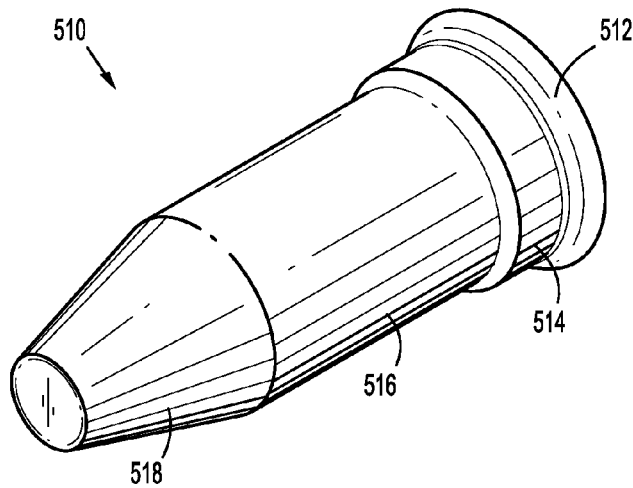
FIG. 35 is a front perspective view of the pivot pin of FIG. 34.
Figure 36:
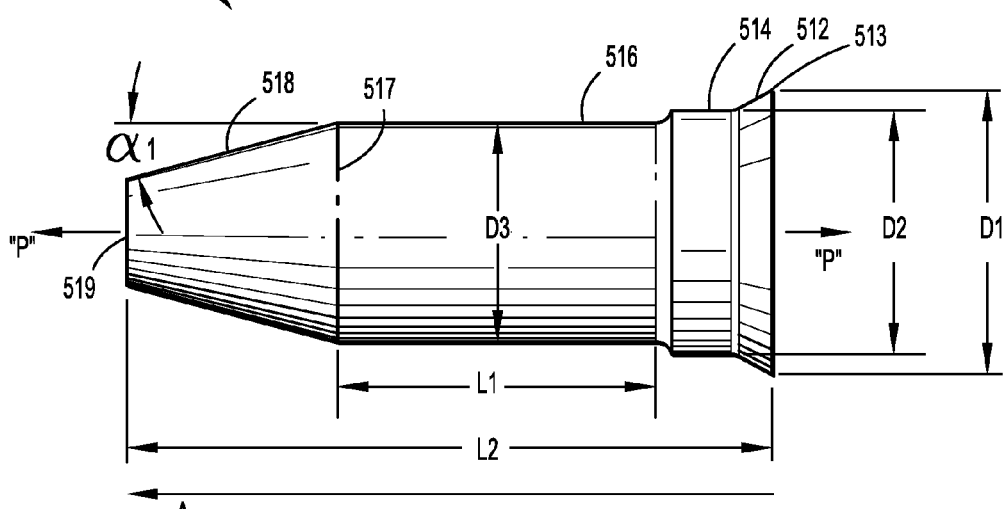
FIG. 36 is a side view of the pivot pin of FIGS. 34 and 35.

With particular reference to FIGS. 34-36, pivot pin 510 includes a head 512, a neck 514, a body 516, and a tip 518. As shown in FIG. 36, head 512 includes a frusto-conical shape and defines a first outer diameter D1 at its widest, proximal-most portion, neck 514 is generally cylindrical (e.g., a majority of neck 514 is a cylinder) and defines a second outer diameter D2, body 516 is cylindrical (e.g., along its entire length L1) and defines a third outer diameter D3, and tip 518 includes a conical (e.g., frusto-conical) shape and extends from a distal end 517 of body 516. An outer surface of tip 518 defines a first angle α1 with respect to a central longitudinal axis "P-P" of pivot pin 510. As shown, the various outer diameters of pivot pin 510 (i.e., D1, D2, and D3) either decrease or remain constant between a proximal-most portion 513 thereof and a distal-most portion 519 thereof. In other words, outer diameters of pivot pin 510 in the proximal-to-distal direction indicated by arrow "A" in FIG. 36 do not increase.

It is envisioned that first diameter D1 defined by head 512 is between about 0.080 inches and about 0.090 inches, second diameter D2 defined by neck 514 is between about 0.070 inches and about 0.075 inches, third diameter D3 defined by body 516 is between about 0.060 inches and about 0.070 inches (e.g., D3 may be equal to about 0.065 inches or 0.066 inches), length L1 of body 516 is between about 0.098 inches and about 0.104 inches, and that first angle α1 is between about 10° and about 20°. It is further envisioned that an entire length L2 of pivot pin 500 is between about 0.190 inches and about 0.120 inches (e.g., L2 may be equal to about 0.193 inches).

Figure 37:
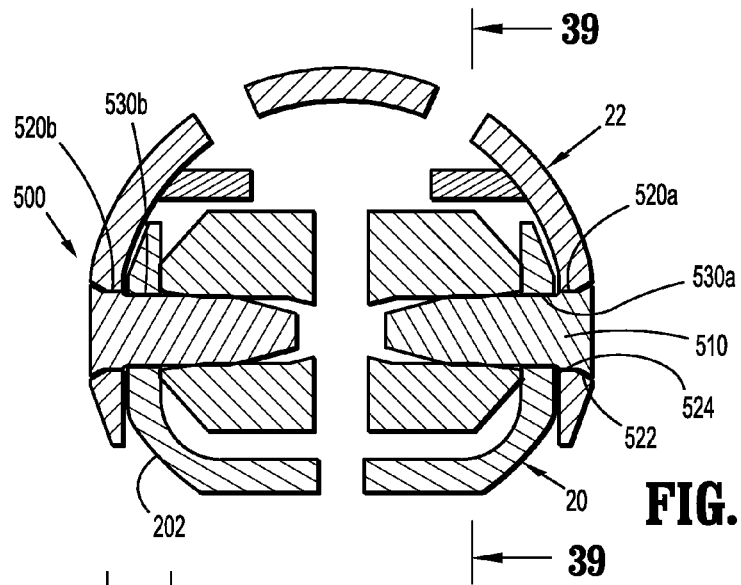
FIG. 37 is a cross-sectional view of the pivot mechanism taken along line 37-37 of FIG. 33.
Figure 38:
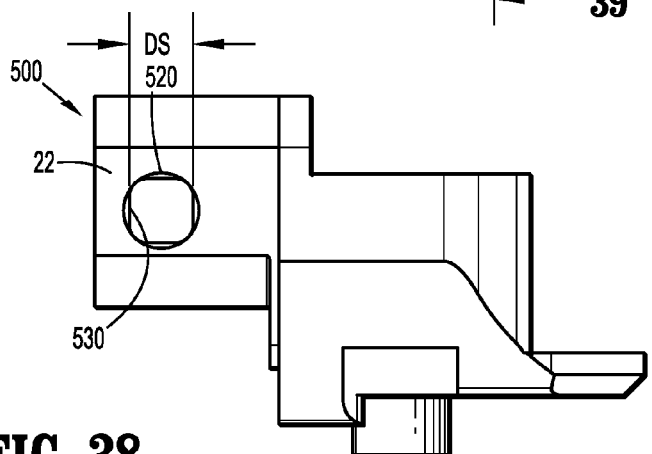
FIG. 38 is a side view of the cartridge assembly engaged with the pivot pin of FIGS. 34-36.
Figure 39:
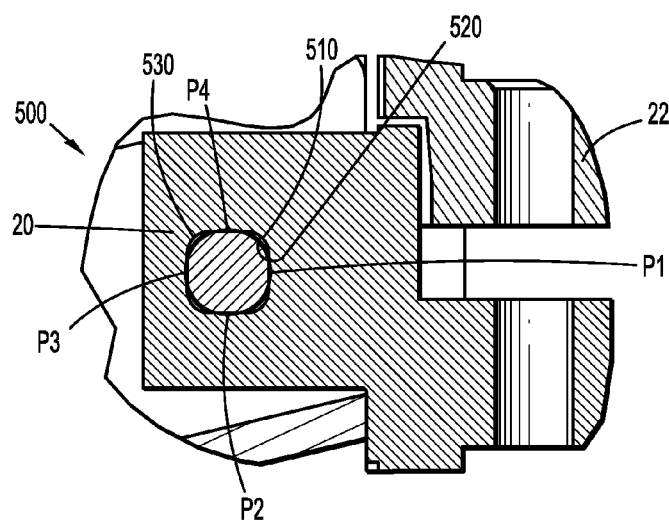
FIG. 39 is a cross-sectional view of the pivot mechanism taken along line 39-39 of FIG. 37.

Referring now to FIGS. 37-39, pivot pin 510 is shown in engagement with apertures 520 and 530. As shown in FIG. 37, each pivot pin 510 extends through aperture 520 of anvil assembly 22 and through aperture 530 of cartridge assembly 20. With particular reference to FIGS. 37 and 38, aperture 520 of anvil assembly 22 is circular. It is envisioned that aperture 520 of anvil assembly 22 includes a wedge portion 522 that matches the shape of head 512, and a cylindrical portion 524 that matches the shape of neck 514. The diameters of wedge portion 522 and cylindrical portion 534 are slightly larger (e.g., between about 0.010 inches and about 0.020 inches) [inventor: please confirm accuracy]. Accordingly, anvil assembly 22 is configured to pivot with respect to pivot pin 510.

Aperture 530 of cartridge assembly 20 is a square-like shape including rounded corners. That is, aperture 530 of cartridge assembly 20 includes four straight sides with adjacent sides connected by rounded portions. In disclosed embodiments, aperture 530 of cartridge assembly 20 includes straight sides having straight or linear portions that are between about 0.0465 inches and about 0.0545 inches, and with adjacent straight portions interconnected by rounded portions each having a radius of between about 0.009 inches and about 0.015 inches. It is further envisioned that the distance DS between opposite sides of aperture 530 of cartridge assembly 20 is between about 0.0615 inches and about 0.0635 inches [inventor: please confirm accuracy].

Body 516 of pivot pin 510 is configured to engage aperture 530 of cartridge assembly 20. Moreover, as discussed above, third diameter D3 defined by body 516 is between about 0.060 inches and about 0.070 inches (e.g., D3 may be equal to about 0.065 inches or 0.066 inches). Thus, in embodiments where diameter D3 of body 516 is larger than the distance DS between opposite sides of aperture 530, interference exists at four points P1-P4 therebetween (see FIG. 39). It is envisioned that that amount of interference (or overlap) is between about 0.0015 inches and about 0.0031 inches. These four points P1-P4 of interference prevent or hinder pivotal movement between pivot pin 510 and cartridge assembly 20. Accordingly, anvil assembly 22 is able to pivot with respect to pivot pin 510 and with respect to cartridge assembly 20.

Additionally, while aperture 520 of anvil assembly 22 is shown and described as being circular, and while aperture 530 of cartridge assembly 20 is shown and described as being square-like, it is envisioned that aperture 520 of anvil assembly 22 is square-like and aperture 530 of cartridge assembly is circular. In such an arrangement, pivot pin 510 is coupled to aperture 520 using an interference fit as described above with respect to aperture 530 having the square-like configuration. This arrangement allows anvil assembly 22 and pivot pin 510 to rotate in unison with respect to cartridge assembly 20. Here, it is envisioned that aperture 530 of cartridge assembly 20 is disposed laterally outward of aperture 520 of anvil assembly 22.

Figure 40:
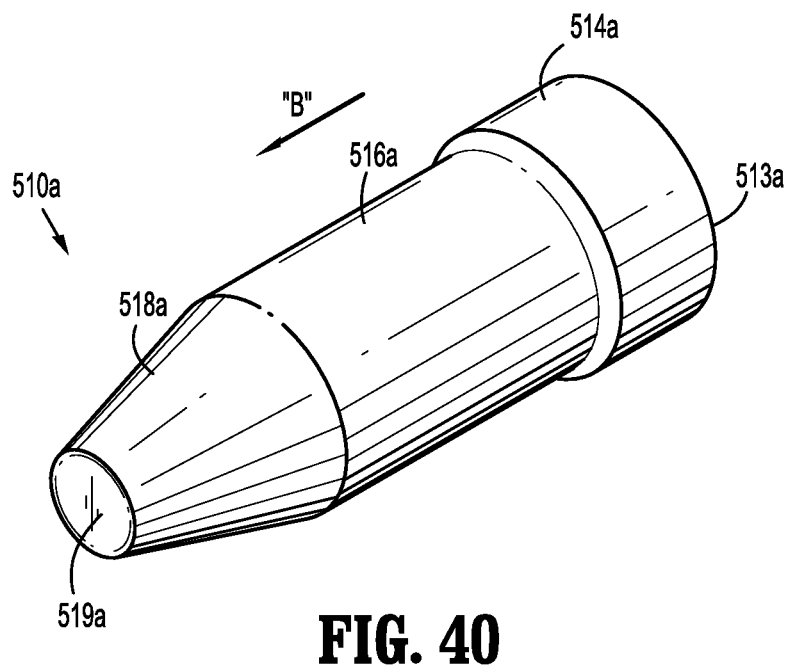
FIG. 40 is a perspective view of a pivot pin of a pivot mechanism in accordance with a further embodiment of the present disclosure.

An alternate embodiment of a pivot pin 510a is shown in FIG. 40. The difference between pivot pin 510a and pivot pin 510 is the lack of a head 512 on pivot pin 510a. That is, pivot pin 510a includes a neck 514a, a body 516a and a tip 518a. Similar to pivot pin 510, the various outer diameters of pivot pin 510a either decrease or remain constant between a proximal-most portion 513a thereof and a distal-most portion 519a thereof. In other words, outer diameters of pivot pin 510a in the proximal to distal direction indicated by arrow "B" in FIG. 40 do not increase. It is envisioned that this head-less pivot pin 510a would allow anvil assembly 22 to move laterally outward (e.g., out of contact with cartridge assembly 20) after insertion of pivot pin 510a through apertures 520 and 530. Such lateral movement of anvil assembly 22 with respect to cartridge assembly 20 would reduce the friction and rubbing therebetween (e.g., during opening and closing of the jaw members), thereby enabling a smoother and less "sticky" operation. By contrast, the head 512 of pivot pin 510 may prevent anvil assembly 22 from moving laterally outward with respect to cartridge assembly 20 after the coupling therebetween (see FIG. 37).

Figure 41:
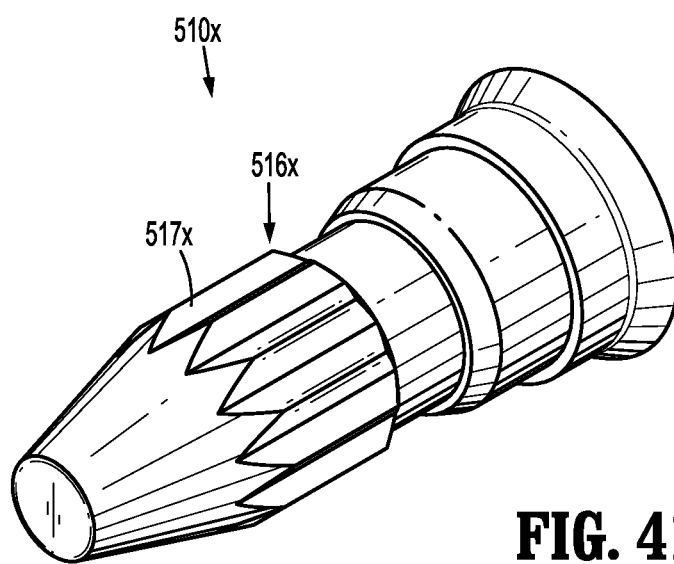
FIG. 41 is a perspective view of another embodiment of a pivot pin.
Figure 42:
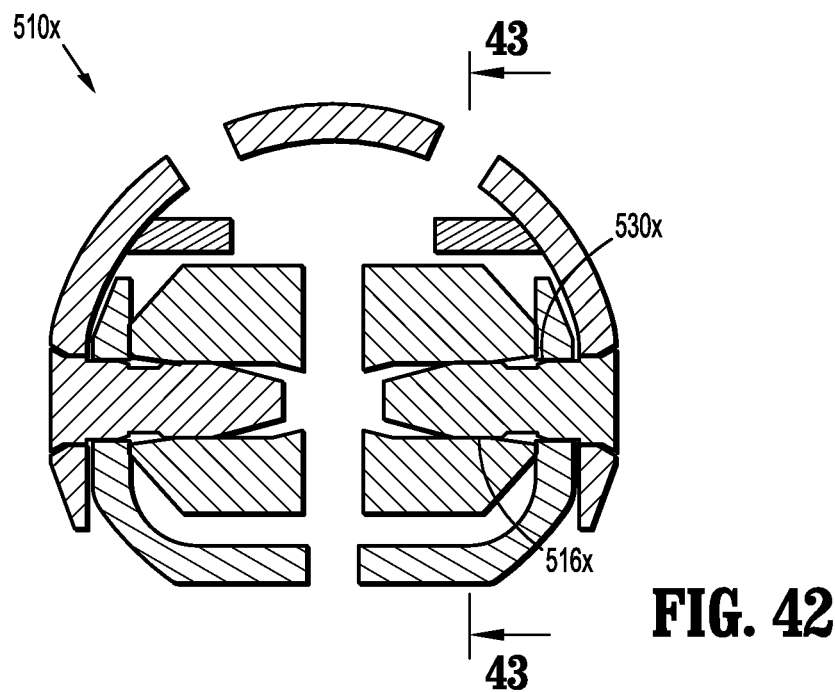
FIG. 42 is a cross-sectional view of the pivot pin of FIG. 41 engaged with a loading unit.
Figure 43:
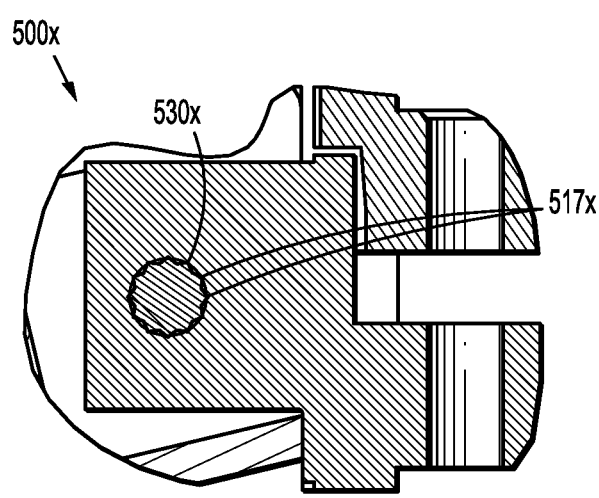
FIG. 43 is a cross-sectional view taken along line 43-43 of FIG. 42.

An alternate embodiment of a pivot mechanism 500x is shown in FIGS. 41-43. The major differences between pivot mechanism 500 discussed above and pivot mechanism 500x of FIGS. 41-43 is the shape of aperture 530 versus the shape of an aperture 530x, and body 516 of pivot pin 510 versus a body 516x of a pivot pin 510x. Specifically, in contrast to the square-like aperture 530 of pivot mechanism 530, aperture 530x of pivot mechanism 500x is round (see FIG. 43). And in contrast to the constant diameter body 516 of pivot pin 510, body 516x of pivot pin 510x is complex with a non-constant diameter and includes a plurality of teeth 517x. With particular reference to FIG. 43, the engagement between teeth 517x and aperture 530x includes a plurality of points of engagement or interference as there are number of teeth 517x. For example, in the illustrated embodiment, there are twelve teeth 517x, and thus twelve points of interference between teeth 517x and aperture 530x versus four points P1-P4 of interference between body 516 of pivot pin 510 and aperture 530.

The disclosed pivot mechanism 500 also facilitates the manufacturability of pivot pin 510, helps ease assembly of surgical stapling device 10 (e.g., loading unit 16 thereof), and helps create a more robust connection between cartridge assembly 20 and anvil assembly 22. For example, the manufacturing of pivot pin 510 is significantly easier and thus less costly than manufacturing pivot pin 510x, e.g., due to the simplicity of body 516. The ease of manufacturability also helps increase the accuracy and tighten the tolerances of pivot pin 510, which results in a more effective, accurate and robust connection between cartridge assembly 20 and anvil assembly 22. As can be appreciated, the ease of manufacturability also decreases the associated costs of manufacturing pivot pin 510 versus pivot pin 510x, for example.

Additionally, relatively low amounts of force to are required insert and remove pivot pin 510 into engagement with and out of engagement from apertures 520, 530 with respect to the insertion and removal forces required to insert and remove pivot pin 510x into and out of engagement with apertures 520x, 530x, for example. Further, the amount of insertion and removal forces required using pivot mechanism 500 are more consistent (i.e., less variable) than with pivot mechanism 500x, for instance.

As can be appreciated, pivot mechanism 500 is usable with various types of surgical instruments, such as a surgical instrument having a cartridge with a stepped tissue contacting surface and/or staples having different sizes therein, such as those described above with regard to FIGS. 4 and 4A, for example.

It is contemplated that individual features of the above described embodiments may be combined without departing from the scope of the present disclosure. Although the illustrative embodiments of the present disclosure have been described herein with reference to the accompanying drawings, the above description, disclosure, and figures should not be construed as limiting, but merely as exemplifications of particular embodiments. For example, although the tool assembly 18, 418 is described as forming a portion of a loading unit, it is envisioned that the tool assembly 18, 418 can be integrally secured to the body 14 of a surgical device 10 (FIG. 1). It is to be understood, therefore, that the disclosure is not limited to the precise embodiments described herein, and that various other changes and modifications may be effected by one skilled in the art without departing from the scope or spirit of the present disclosure.

The invention claimed is:

1. A pivot mechanism for use with a surgical device, the pivot mechanism comprising:
a first jaw member including at least one circular aperture;
a second jaw member including at least one square-like aperture; and
a pivot pin configured to engage the at least one circular aperture of the first jaw member and the at least one square-like aperture of the second jaw member such that the first jaw member is pivotably coupled to the second jaw member;
wherein the at least one circular aperture of the first jaw member is disposed laterally outward of the at least one square-like aperture of the second jaw member.

2. The pivot mechanism according to claim 1, wherein the at least one circular aperture of the first jaw member includes two circular apertures.

3. The pivot mechanism according to claim 1, wherein the at least one square-like aperture of the second jaw member includes two square-like apertures.

4. The pivot mechanism according to claim 1, wherein the at least one square-like aperture of the second jaw member includes four linear walls with adjacent linear walls interconnected by a rounded portion.

5. The pivot mechanism according to claim 1, wherein the pivot pin includes a head at a proximal portion, a tip at a distal portion, and a body between the head and the tip, an entirety of the body includes a constant outer diameter.

6. The pivot mechanism according to claim 5, wherein the body is in contact with the tip.

7. The pivot mechanism according to claim 6, wherein an entirety of the tip is conical.

8. The pivot mechanism according to claim 1, wherein the first jaw member is an anvil assembly and the second jaw member is a cartridge assembly.

9. A surgical device, comprising:
a handle assembly;
an elongated body extending distally from the handle assembly;
a loading unit disposed adjacent a distal end of the elongated body, the loading unit including a first jaw member having a circular aperture, and a second jaw member having a square-like aperture; and
a pivot pin disposed in mechanical cooperation with the circular aperture and the square-like aperture;
wherein the circular aperture of the first jaw member is disposed laterally outward of the square-like aperture of the second jaw member.

10. The surgical device according to claim 9, wherein a body of the pivot pin is disposed in mechanical cooperation with the square-like aperture, and wherein an entirety of the body has a cylindrical configuration.

11. The surgical device according to claim 9, wherein the square-like aperture of the second jaw member includes four linear walls with adjacent linear walls interconnected by a rounded portion.

12. The surgical device according to claim 9, wherein the pivot pin includes a head at a proximal portion, a tip at a distal portion, and a body disposed therebetween, an entirety of the body having a uniform outer diameter.

13. The surgical device according to claim 9, wherein the first jaw member is an anvil assembly and the second jaw member is a cartridge assembly.

14. A pivot mechanism for use with a surgical device, the pivot mechanism comprising:
a first jaw member including at least one circular aperture defining a diameter; and a second jaw member including at least one square-like aperture defining a first distance between two opposite walls, wherein the diameter is larger than the first distance, and wherein the first jaw member and the second jaw member are pivotable about a common pivot axis that extends through the at least one circular aperture and the at least square-like aperture.

15. The pivot mechanism according to claim 14, further comprising a pivot pin configured to engage the at least one circular aperture of the first jaw member and the at least one square-like aperture of the second jaw member such that the first jaw member is pivotably coupled to the second jaw member.

16. The pivot mechanism according to claim 14, wherein the square-like aperture includes two sets of parallel walls.

\* \* \* \* \*